United States Patent
Branch et al.

(10) Patent No.: US 9,610,038 B2
(45) Date of Patent: Apr. 4, 2017

(54) APPARATUS AND METHOD FOR EVALUATING JOINT PERFORMANCE

(71) Applicant: Thomas P Branch, Atlanta, GA (US)

(72) Inventors: Thomas P Branch, Atlanta, GA (US); Alexander Sattler, Jr., Marietta, GA (US); Eric Branch, Alexander City, GA (US)

(73) Assignee: ERMI, INC., Atlanta, GA (US)

( * ) Notice: Subject to any disclaimer, the term of this patent is extended or adjusted under 35 U.S.C. 154(b) by 0 days.

(21) Appl. No.: 14/271,712

(22) Filed: May 7, 2014

(65) Prior Publication Data

US 2015/0011915 A1    Jan. 8, 2015

Related U.S. Application Data

(60) Continuation of application No. 12/797,324, filed on Jun. 9, 2010, now Pat. No. 8,753,294, which is a division of application No. 11/457,443, filed on Jul. 13, 2006, now Pat. No. 7,753,862.

(60) Provisional application No. 60/699,003, filed on Jul. 13, 2005, provisional application No. 60/786,447, filed on Mar. 27, 2006.

(51) Int. Cl.
*A61B 5/00* (2006.01)
*A61B 5/107* (2006.01)

(52) U.S. Cl.
CPC .......... *A61B 5/4528* (2013.01); *A61B 5/1071* (2013.01); *A61B 5/4533* (2013.01); *A61B 5/702* (2013.01); *A61B 5/6828* (2013.01); *A61B 5/6829* (2013.01); *A61B 5/6831* (2013.01)

(58) Field of Classification Search
CPC .... A61B 5/1071; A61B 5/4533; A61B 5/4528
See application file for complete search history.

(56) References Cited

U.S. PATENT DOCUMENTS

| | | | |
|---|---|---|---|
| T100,602 I4 * | 5/1981 | Roley et al. | 600/595 |
| 4,586,495 A * | 5/1986 | Petrofsky | 602/2 |
| 4,727,860 A | 3/1988 | McIntyre | |
| 4,825,852 A * | 5/1989 | Genovese et al. | 601/34 |
| 4,834,073 A * | 5/1989 | Bledsoe et al. | 601/34 |
| 4,909,262 A * | 3/1990 | Halpern et al. | 600/587 |
| 4,930,497 A * | 6/1990 | Saringer | 601/34 |
| 5,027,799 A * | 7/1991 | Laico et al. | 602/20 |

(Continued)

FOREIGN PATENT DOCUMENTS

WO    8804536    6/1988

OTHER PUBLICATIONS

International Preliminary Report on Patentability in PCT/US2006/027376, dated Oct. 11, 2007, 26 pages.

(Continued)

*Primary Examiner* — Michael C Stout
(74) *Attorney, Agent, or Firm* — Lempia Summerfield Katz LLC

(57) ABSTRACT

The present invention is generally directed to apparatuses and methods for evaluating the amount of "play" in a joint. In one embodiment, an apparatus is provided that quantifies the rotation of the tibia in response to a known torque. The apparatus is configured to minimize the influence of other joints on the rotation analysis. Other embodiments provide data related to movement of the tibia in other degrees of freedom.

2 Claims, 19 Drawing Sheets

(56) References Cited

U.S. PATENT DOCUMENTS

| | | | | |
|---|---|---|---|---|
| 5,228,432 | A * | 7/1993 | Kaiser et al. | 601/34 |
| 5,335,674 | A * | 8/1994 | Siegler | 600/595 |
| 5,382,225 | A * | 1/1995 | Sutcliffe | 602/24 |
| 5,399,147 | A * | 3/1995 | Kaiser | 601/34 |
| 5,402,800 | A * | 4/1995 | Hollis | 600/592 |
| 5,435,321 | A * | 7/1995 | McMillen et al. | 600/595 |
| 5,645,079 | A * | 7/1997 | Zahiri et al. | 5/610 |
| 5,813,988 | A * | 9/1998 | Alfano | A61B 5/0073 356/432 |
| 5,954,701 | A | 9/1999 | Matalon | A61M 25/0693 604/272 |
| 5,995,866 | A * | 11/1999 | Lemelson | A61B 18/20 250/461.2 |
| 6,463,309 | B1 * | 10/2002 | Ilia | A61B 5/0059 382/128 |
| 6,599,255 | B2 * | 7/2003 | Zhang | 600/587 |
| 6,652,461 | B1 * | 11/2003 | Levkovitz | A61B 8/04 128/916 |
| 7,041,069 | B2 * | 5/2006 | West | 601/5 |
| 7,628,766 | B1 * | 12/2009 | Kazerooni et al. | 602/16 |
| 2002/0111634 | A1 * | 8/2002 | Stoianovici | A61B 19/26 606/129 |
| 2004/0003468 | A1 | 1/2004 | Mitsuishi | |
| 2004/0260208 | A1 * | 12/2004 | Laprade et al. | 600/595 |
| 2005/0168980 | A1 * | 8/2005 | Dryden | A61B 5/489 362/230 |
| 2005/0177201 | A1 * | 8/2005 | Freeman | A61N 1/0529 607/46 |
| 2005/0222573 | A1 * | 10/2005 | Branch et al. | 606/86 |
| 2005/0228291 | A1 * | 10/2005 | Chance | A61B 5/0073 600/476 |
| 2005/0287072 | A1 * | 12/2005 | Contag | A01K 67/0275 424/9.6 |
| 2006/0020279 | A1 * | 1/2006 | Chauhan | A61B 19/2203 606/167 |
| 2006/0129037 | A1 * | 6/2006 | Kaufman | A61B 5/14535 600/322 |
| 2006/0129038 | A1 * | 6/2006 | Zelenchuk | A61B 5/14535 600/322 |
| 2006/0173351 | A1 * | 8/2006 | Marcotte | A61B 5/0059 600/473 |
| 2006/0229531 | A1 * | 10/2006 | Goldberger | A61B 5/1427 600/573 |
| 2006/0293643 | A1 * | 12/2006 | Wallace | A61B 19/5244 606/1 |
| 2007/0040907 | A1 * | 2/2007 | Kern | A61B 5/0059 348/77 |
| 2007/0073156 | A1 * | 3/2007 | Zilberman | A61B 5/0064 600/473 |
| 2007/0123997 | A1 * | 5/2007 | Herr et al. | 623/27 |
| 2007/0206099 | A1 * | 9/2007 | Matsuo | G06K 9/00033 348/208.12 |
| 2007/0253607 | A1 * | 11/2007 | Higuchi | G06K 9/00026 382/124 |
| 2008/0027317 | A1 * | 1/2008 | Wood | A61B 5/0059 600/427 |
| 2008/0137926 | A1 * | 6/2008 | Skinner | G06K 9/34 382/131 |
| 2008/0146915 | A1 * | 6/2008 | McMorrow | A61B 5/1422 600/424 |
| 2008/0195043 | A1 * | 8/2008 | Schwach | A61B 5/0059 604/116 |
| 2008/0275396 | A1 * | 11/2008 | Neerken | A61B 5/0059 604/116 |
| 2008/0306392 | A1 * | 12/2008 | Satoguchi | A61B 5/0059 600/479 |
| 2009/0021739 | A1 * | 1/2009 | Tsujita | A61B 1/00163 356/407 |
| 2009/0118670 | A1 * | 5/2009 | Neerken | A61B 5/0059 604/116 |
| 2009/0149867 | A1 * | 6/2009 | Glozman | A61B 17/3478 606/130 |
| 2009/0245601 | A1 * | 10/2009 | Cohen | A61B 5/489 382/128 |
| 2009/0248038 | A1 * | 10/2009 | Blumenkranz | A61B 19/2203 606/130 |
| 2009/0248041 | A1 * | 10/2009 | Williams | A61B 8/12 606/130 |
| 2009/0275823 | A1 * | 11/2009 | Ayati | A61B 5/1411 600/424 |
| 2010/0010505 | A1 * | 1/2010 | Herlihy | A61B 19/201 606/130 |
| 2010/0172567 | A1 * | 7/2010 | Prokoski | A61B 5/0064 382/132 |

OTHER PUBLICATIONS

N.J. Dahlkvist et al., "Objective Measurement of Knee Laxity and Stiffness with Reference to Knee Injury Diagnosis, Part 1: Design Considerations and Apparatus", Proceedings of the Institution of Mechanical Engineers, Journal of Engineering in Medicine, 1990, pp. 75-82, vol. 204.
Office Communication in European Patent Application No. 06 787 304.2, dated Apr. 4, 2012, 5 pages.
Office Communication in European Patent Application No. 06 787 304,2, dated Feb. 16, 2015, 4 pages.
Summons to attend oral proceedings in European Patent Application No. 06 787 304.2, dated Mar. 30, 2016, 9 pages.
T.G. Olmstead et al., "Effect of Muscular Activity on Valgus/Varus Laxity and Stiffness of the Knee", Journal of Biomechanics, 1986, pp, 565-577, vol. 19, No. 8.

* cited by examiner

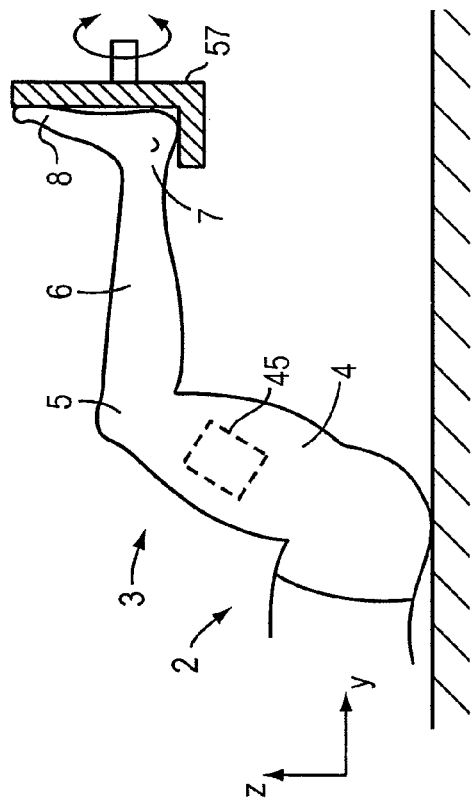
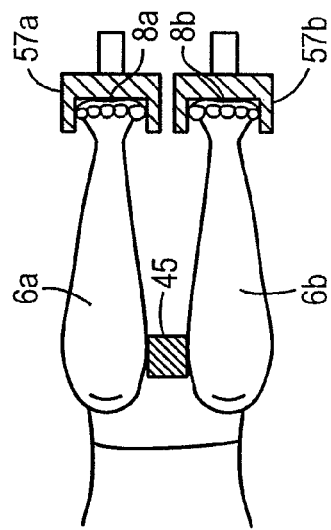
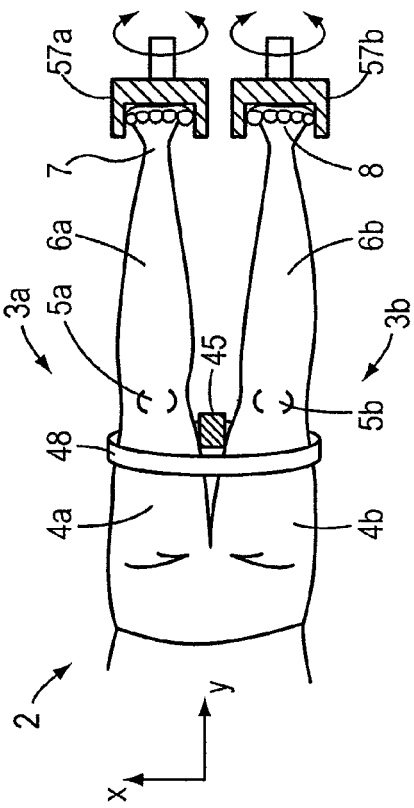
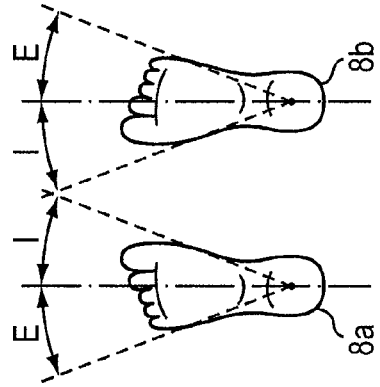

APPARATUS AND METHOD FOR EVALUATING JOINT PERFORMANCE

CROSS-REFERENCE TO RELATED APPLICATIONS

This application is a continuation of U.S. application Ser. No. 12/797,324, filed Jun. 9, 2010, entitled "Apparatus and Method for Evaluating Ligaments", which is a divisional of U.S. application Ser. No. 11/457,443, filed Jul. 13, 2006, now U.S. Pat. No. 7,753,862, issued 2010 Jul. 13, entitled "Apparatus and Method for Evaluating Ligaments", which claims the full benefit and priority of U.S. provisional Application No. 60/699,003, filed Jul. 13, 2005, entitled "Apparatus and Method of Use for Determining Limb Rotation", and U.S. Provisional Application No. 60/786,447, filed Mar. 27, 2006, entitled "Apparatus and Method For Evaluating Ligaments." The entire contents of all such applications are incorporated by reference into this application.

FIELD OF THE INVENTION

The present invention relates to apparatuses and methods for evaluating the performance of a joint. More particularly, the present invention provides apparatuses and methods for quantifying the amount of movement allowed by a joint to aid in the diagnosis of and treatment for ligament damage.

BACKGROUND

The knee is composed of the femur or thigh bone, the tibia or shin bone and the patella or knee cap. They are connected by fibrous structures called ligaments which allow a certain amount of 'joint play' to exist between the bone structures. When this 'joint play' is increased or decreased an abnormal or pathological condition exists in the knee. Attempts have been made in the past to quantify this increase or decrease in joint play' of the knee with limited success.

An injury to the knee can cause damage to one or more of the structures of the knee causing an increase in the 'joint play' of the knee. This increase in 'joint play' can create the sensation to the patient that the knee is slipping or 'coming out of joint'. Commonly, this sensation described by the patient is referred to as the feeling of 'joint instability'. The ability of the two bones to actually 'come out of joint' is related to the length of the fibrous structures or ligaments which connect the two bones together as well as the shape and size of the two bones (or three). The ability of the bones to 'come out of joint' or become unstable is related to the amount of stretch or the amount of increased lengthening of each ligament, the number of ligaments involved, and damage to other support structures of the knee such as the bone itself and the menisci. Accurate measurement of this increased ligament length is critical to restore the knee to as close to its original functional and anatomical state as possible.

Currently, there are only manual tests used by clinicians to aid in the diagnosis of ligament damage or increased (decreased) joint play. As an example, there are three manual tests to evaluate the increased joint play associated with an ACL tear—the Lachman's test, the Pivot Shift test and the Anterior Drawer Test. All of these tests suffer from the clinician's subjective evaluation of both the extent of the ligament lengthening and the change in the compliance or stretchiness of the ligament.

The Lachman's test is performed by laying the patient in a supine position and bending the knee at approximately 20 to 30 degrees. The clinician places a hand on the patient's upper thigh and his other hand below the upper part of the patient's calf muscle. Pressure is applied under the patient's calf and down on the patient's thigh such that translation between the tibia and femur occurs.

Similar to the Lachman's test, the pivot shift test begins by positioning the patient on his back. The knee is flexed (x-axis rotation) and a valgus (z-axis rotation) force and an internal rotation (y-axis rotation) force is applied to the knee as the knee is brought into full extension (x-axis rotation). The clinician feels for an abnormal internal rotation (y-axis rotation) and anterior translation (z-axis translation) of the tibia with respect to the femur. This shift is felt to represent the relative increased translation (z-axis translation) of the lateral side of the knee with respect to the increased translation (z-axis translation) of the medial side of the knee. Furthermore, the point of sudden shift represents the point at which the back part of the tibia bone slides in front of the radius of curvature of the curved end of the femur. The clinician subjectively rates the pivot shift as Grade I, Grade II or Grade III depending upon the degree of rotational and translational shift felt during the test. This test is difficult to perform, difficult to teach and difficult to quantify.

Finally, the anterior drawer test is performed with the patient lying on his back and his knee bent to 90 degrees. With the patient's foot supported by a table or chair, the clinician applies pressure to the knee using her thumbs. This test is graded based upon the amount or extent of anterior translation along the z-axis of the tibia with respect to the femur. Grade I has 0 to 5 mm of anterior translation (z-axis translation), Grade II has 6 to 10 mm of anterior translation, and Grade III has 11 to 15 mm of translation.

To diagnose an injured ACL using the described tests, the clinician must determine whether the knee feels "abnormal." Thus, the accuracy of an ACL injury diagnosis using currently known tests depends on the skill and experience of the clinician. A misdiagnosis can lead to unnecessary delay in treatment, thereby placing the patient at increased risk for further damage to the knee.

There are manual tests for the LCL, MCL and the PCL. Each manual test relies on grading the extent of the ligament lengthening into three categories. There is no effort to grade the compliance of the ligament; however, the expert clinician will describe the ligament in terms of its 'feel'. The more ligaments and structures that are damaged; the more complex it becomes to perform a knee examination using the subjective manual exams.

There have been multiple attempts in the past to instrument the knee and quantify or measure the change in the structure of the knee after ligament damage. Only one device has attempted to accurately quantify the extent or relative displacement and compliance a ligament in the knee. The KT-1000 and the KT-2000 Medmetric® by measure the anterior-posterior translation of the tibia with respect to the femur along the z-axis. These devices attempt to quantify the findings found when the clinician uses the Lachman's test and the Anterior Drawer Test. Force is applied to a handle on the device which measures force and signals to the clinician the amount of force with a low pitched sound for the 15 pound force, a higher pitched sound for the 20 pound force. This force pulls anteriorly along the z-axis through a strap that wraps underneath the calf. The measurement of the translation uses a technique measuring the relative motion of a pad on the anterior tibia with respect to a pad placed on the patella. This device does not measure relative displacement or compliance in any of the other degrees of freedom previously described in the knee. Furthermore, the quantified results of the KT-1000 or KT-2000 have not been correlated with patient satisfaction where as the subjective Pivot Shift test has bee correlated with patient satisfaction.

Accordingly, there is a need for an accurate, objective, reliable and reproducible measure of the impact of damage to the ACL as well as other ligaments and structures in the knee that can be used in the clinical setting on patients. For example, since an injury to the ACL produces both an increase in anterior translation (z-axis translation) and rotation (y-axis rotation), an objective measure of these changes would both aid in the diagnosis of the injury as well as verify its restoration after ligament reconstruction surgery. Additionally, measurement of displacement and compliance around different degrees of freedom in the knee would help objectively describe the individual and complex changes to 'joint play' that occur with an injury to the knee. A need exists for systems and methods that can provide accurate, reproducible and objective data on the changes in 'joint play' that occur with an injured knee compared to their noinial knee and to the population as a whole such that the clinician can achieve patient satisfaction with focused, biomechanical and proven surgical interventions individualized for that injury and for that knee across the entire population of damaged knees.

SUMMARY OF THE INVENTION

The following summary is not an extensive overview and is not intended to identify key or critical elements of the apparatuses, methods, systems, processes, and the like, or to delineate the scope of such elements. This Summary provides a conceptual introduction in a simplified form as a prelude to the more-detailed description that follows.

The above and other needs are met by the present invention which provides apparatuses and methods for evaluating the amount of play in a joint.

In one aspect of the invention, an apparatus for evaluating the rotational performance of a patient knees is provided where the patient has two legs and each leg has a femur, knee, tibia, ankle and a foot. The apparatus includes: a frame having a base configured to be placed on a support surface and a support column attached relative to the base and extending substantially perpendicular there from; a transverse member attached relative to the support column within a plane substantially parallel to the base and perpendicular to the support column; a first pivot assembly attached relative to the transverse member and configured to transfer a torque to a first tibia of the patient by rotating an associate first foot about an axis substantially aligned with the longitudinal axis of the first tibia; a first angle measuring device attached relative to the first assembly and configured to measure angular displacement of the first pivot assembly in response to the torque; a second pivot assembly attached relative to the transverse member and configured to transfer a torque to a second tibia of the patient by rotating an associate second foot about an axis substantially aligned with the longitudinal axis of the second tibia; and a second angle measuring device attached relative to the second pivot assembly and configured to measure angular displacement of the second pivot assembly in response to the torque.

In another aspect of the invention, an apparatus for evaluating the rotation performance of a patient's knees is provided. The apparatus includes: a frame having a cross member attached relative to a spine member; a plurality of thigh positioning posts releasably attached relative to said cross member and configured to secure said two thighs of the patient; a carriage configured to move along at least a portion of the length of the spine member; a first pivot assembly attached relative to the carriage and configured to transfer a torque to a first tibia of the patient by rotating an associate first foot about an axis substantially aligned with the longitudinal axis of the first tibia; a first angle measuring device attached relative to the first assembly and configured to measure angular displacement of the first pivot assembly in response to the torque; a second pivot assembly attached relative to the carriage and configured to transfer a torque to a second tibia of the patient by rotating an associate second foot about an axis substantially aligned with the longitudinal axis of the second tibia; and a second angle measuring device attached relative to the second pivot assembly and configured to measure angular displacement of the second pivot assembly in response to the torque.

In a further aspect, an apparatus for evaluating the performance of a patient's knee in two degrees of freedom is provided. The apparatus includes: a frame having a cross member attached relative to a spine member; a plurality of thigh positioning posts releasably attached relative to the cross member and configured to secure the thigh of the patient; a carriage configured to move along at least a portion of the length of the spine member; a first pivot assembly pivotably attached relative to the carriage and configured to transfer a torque to the tibia causing movement of the tibia relative to the femur in a first degree of freedom; a first angle measuring device attached relative to the first pivot assembly and configured to measure angular displacement of the first pivot assembly in response to the torque; a second pivot assembly pivotably attached relative to the carriage and configured to transfer a second torque to the tibia causing movement of the tibia relative to the femur in a second degree of freedom; and a second angle measuring device attached relative to the second pivoting assembly and configured to measure angular displacement of the second pivot assembly in response to the second torque.

In another aspect of the invention, a method for evaluating the performance of a knee of a patient is provided. This method includes the steps of: positioning a patient supine with the knee bent; positioning the foot into an AFO rotatably attached to a frame such that the axis of rotation of the AFO is in substantial alignment with the longitudinal axis of the tibia; rotating the AFO by applying a torque; capturing data related to the rotation of the AFO.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

FIG. 1 is an illustrative view of a patient's legs and a portion of an embodiment of the present invention. This view may be considered a side plan view of a patient in a supine position looking at the patient's right side.

FIGS. 2 and 4 are illustrative views of a patient's legs and a portion of embodiments of the present invention. These views may be considered a view looking down on a patient in a supine position.

FIG. 3 is a illustrative view of a patient's feet showing internal ("I") and external ("E") rotation of the feet and associated tibia (not shown) in accordance with an embodiment of the present invention.

Figure 8:
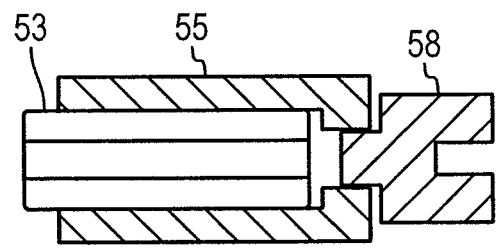

FIG. 8 is section view of the socket 55 and conversion socket 58 thereby exposing the shaft 53 in accordance with an embodiment of the present invention.

Figure 9:
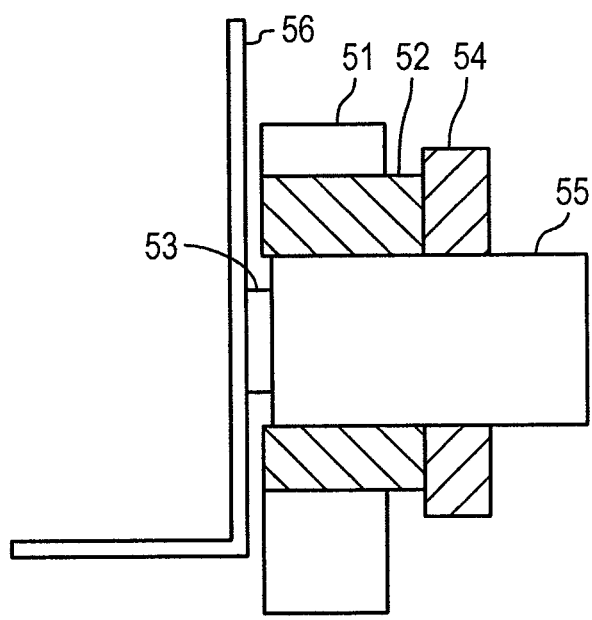

FIG. 9 is a section view of the bushing retainer 51, bushing 52, and collar 54 thereby exposing the socket 55 and a portion of the shaft 53 in accordance with an embodiment of the present invention.

Figure 10:
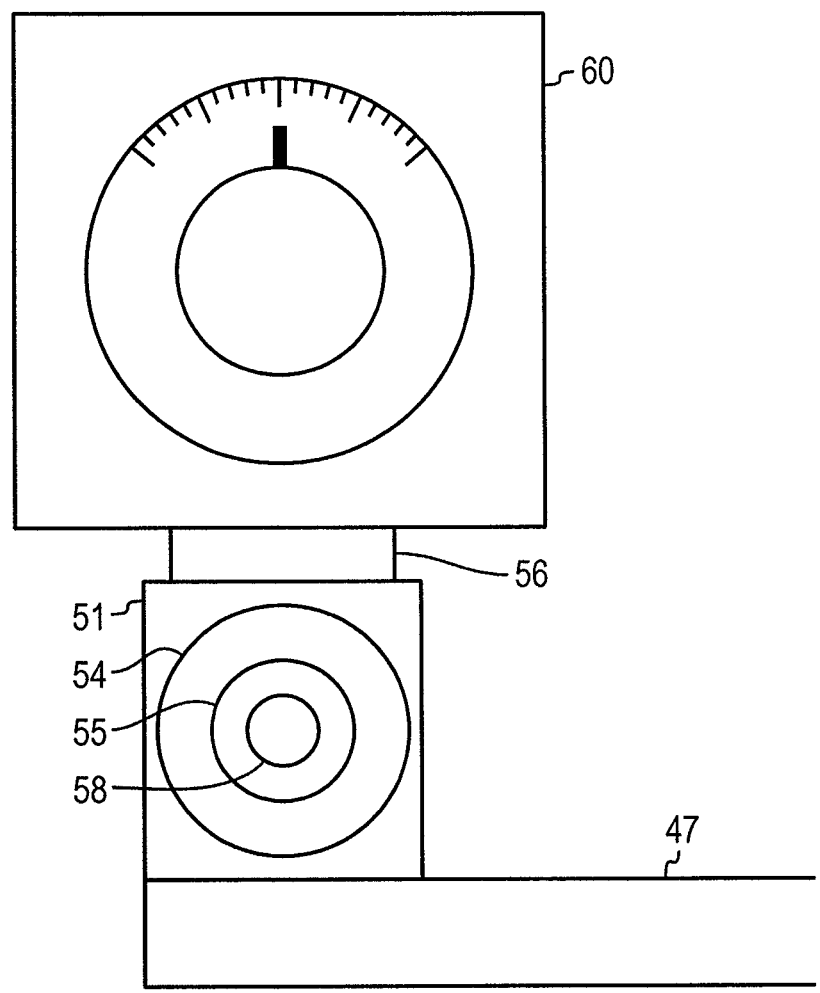

FIG. 10 is a drawing illustrating the angle measurement device 60 in accordance with an embodiment of the present invention.

Figure 11:
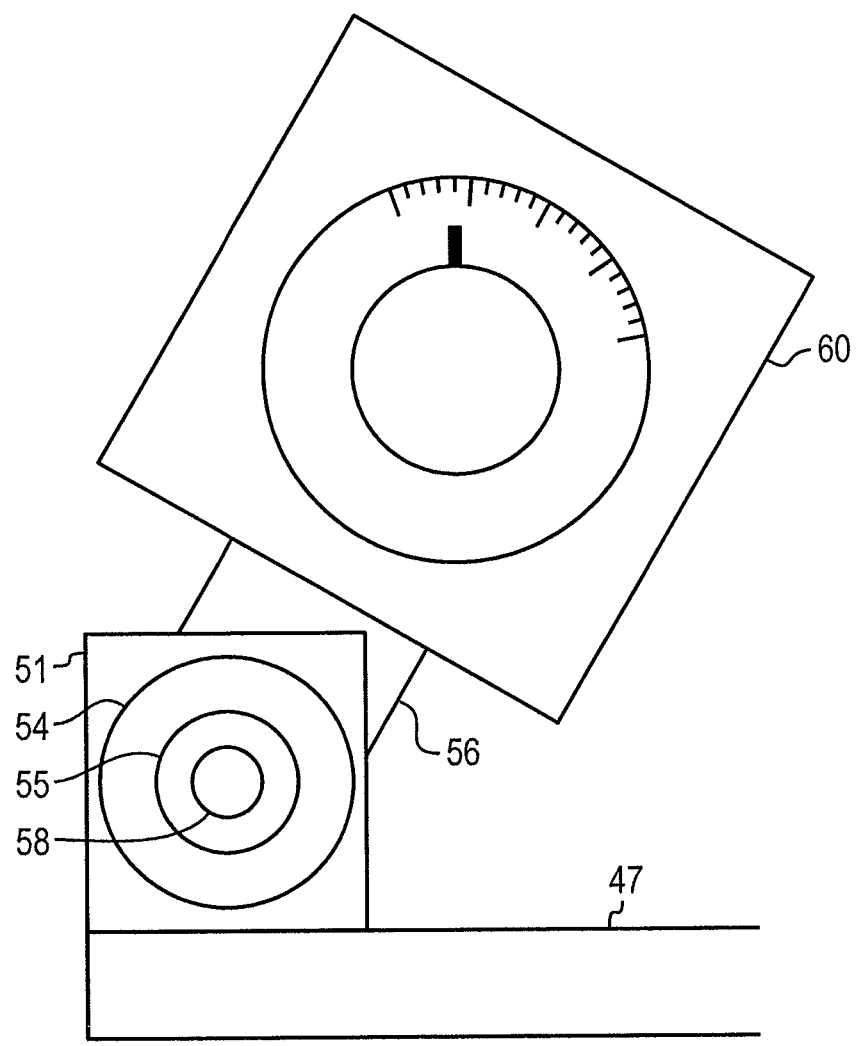

FIG. 11 is a drawing of the angle measurement device 60 in FIG. 10 with the pivoting assembly rotated clockwise to illustrate the effect on the angle measurement device 60.

Figure 12:
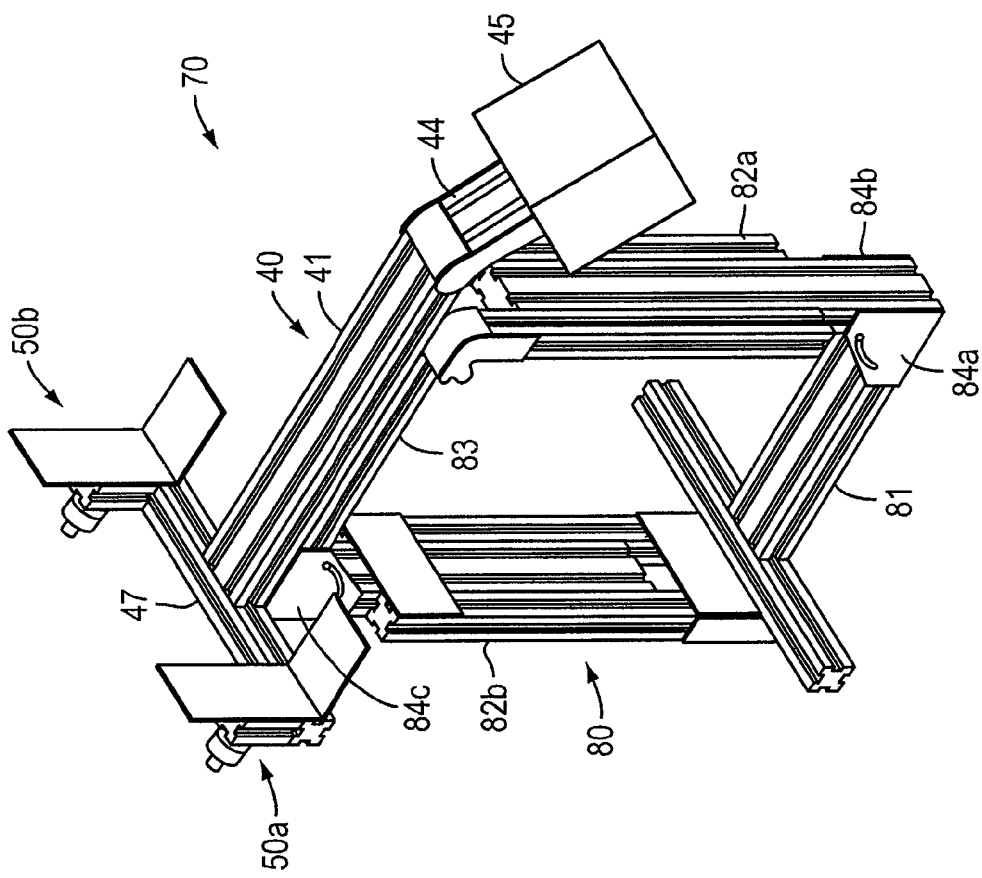

FIG. 12 is drawing of folding assembly 70 in accordance with an embodiment of the present invention.

Figure 13:
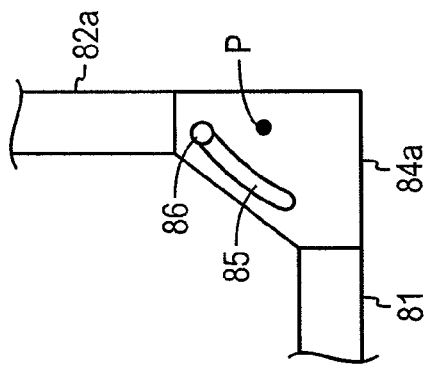

FIG. 13 is a drawing of a portion of the folding assembly 70 illustrating exemplary plate bracket 84a.

Figure 14:
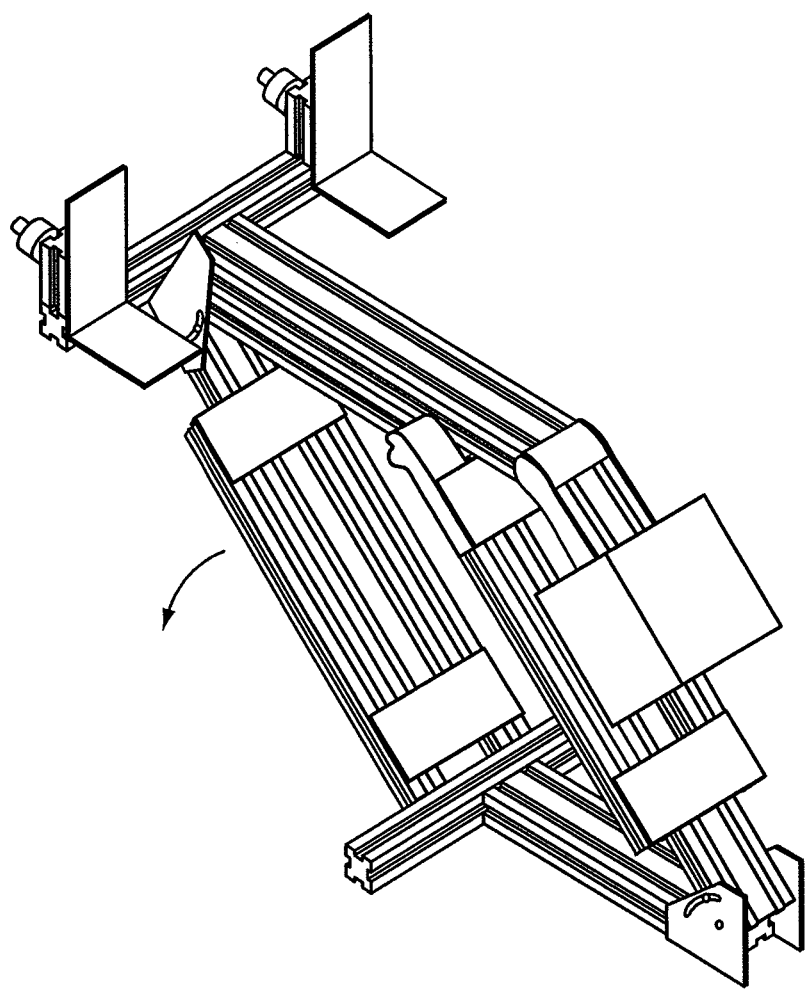

FIG. 14 is a drawing showing a folding assembly 70 partially folded in accordance with an embodiment of the present invention.

Figure 15:
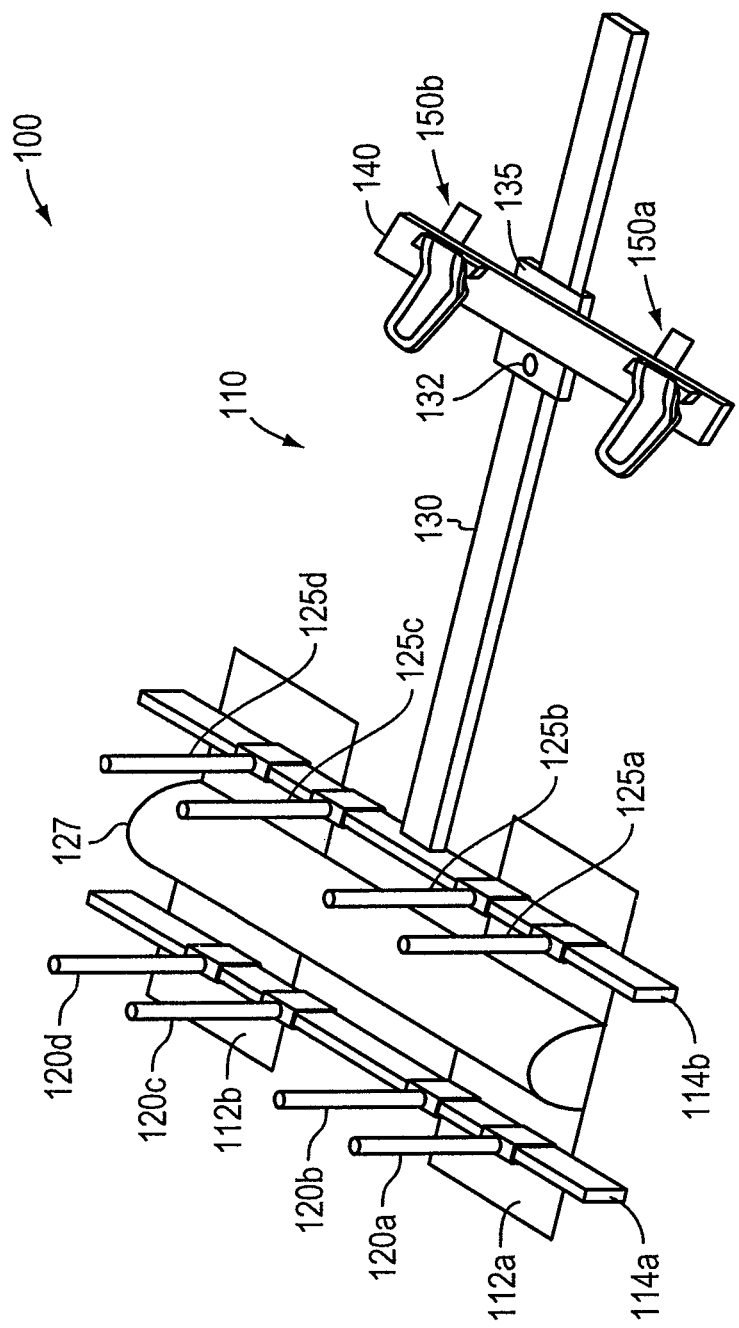

FIG. 15 is a drawing illustrating apparatus 100 in accordance with an embodiment of the present invention.

Figure 16:
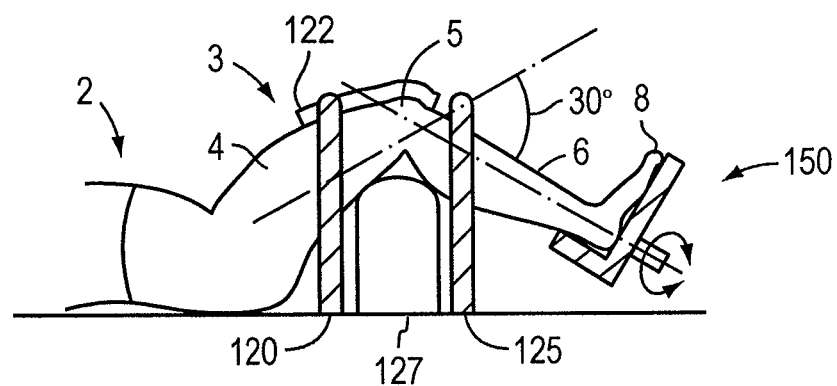
Figure 17:
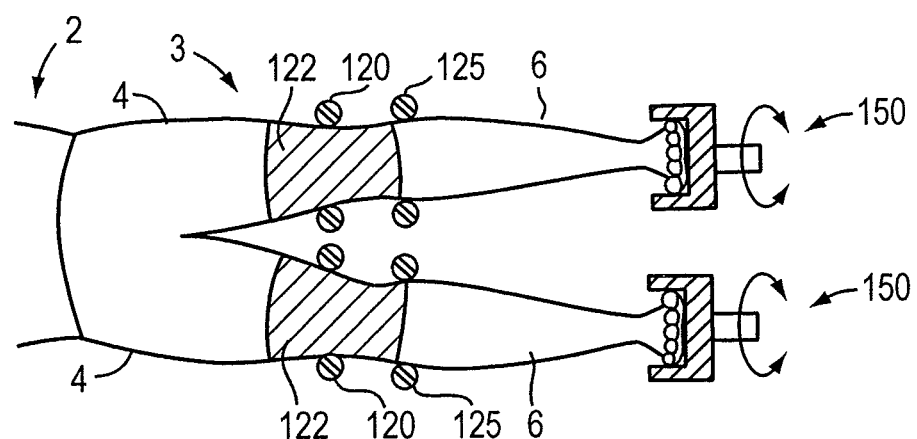
Figure 18:
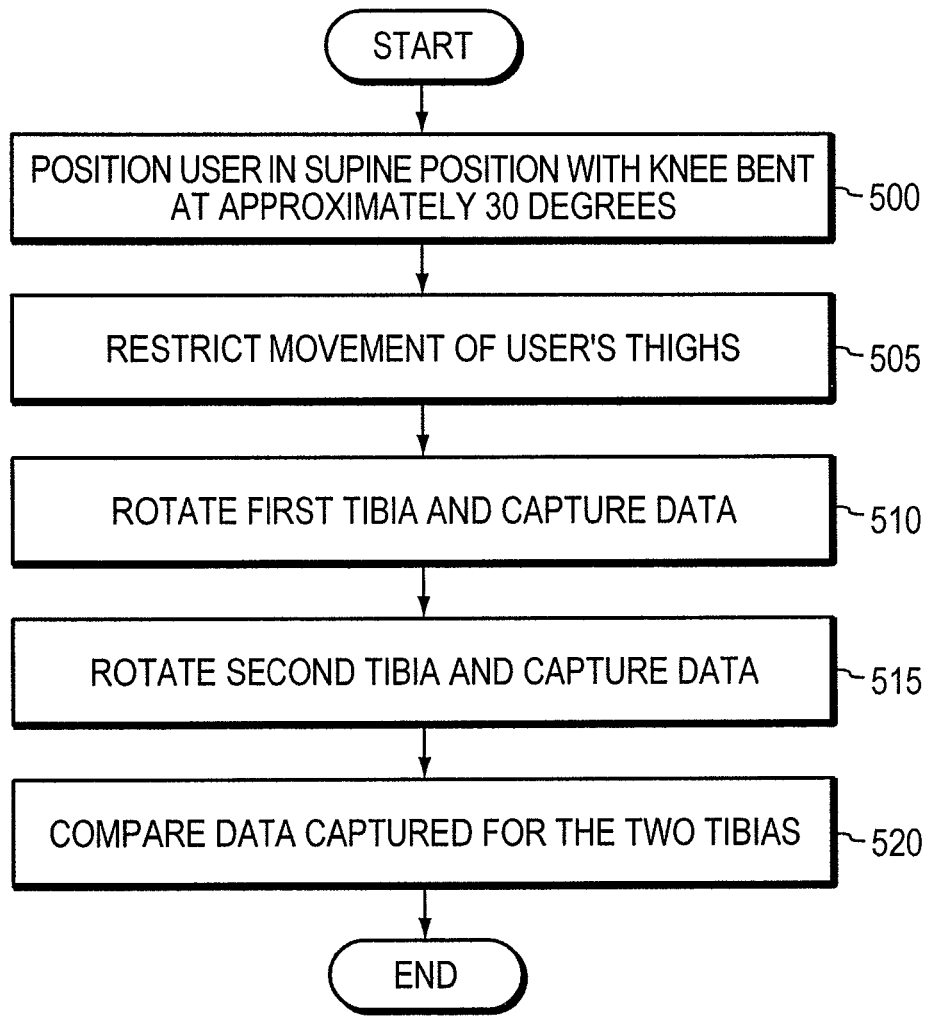

FIGS. 16 and 17 are illustrative drawings of a portion of a patient and a portion of apparatus 100 in accordance with an embodiment of the present invention FIG. 18 is a flow chart illustrating steps of an exemplary method in accordance with an embodiment of the present invention.

Figure 19:
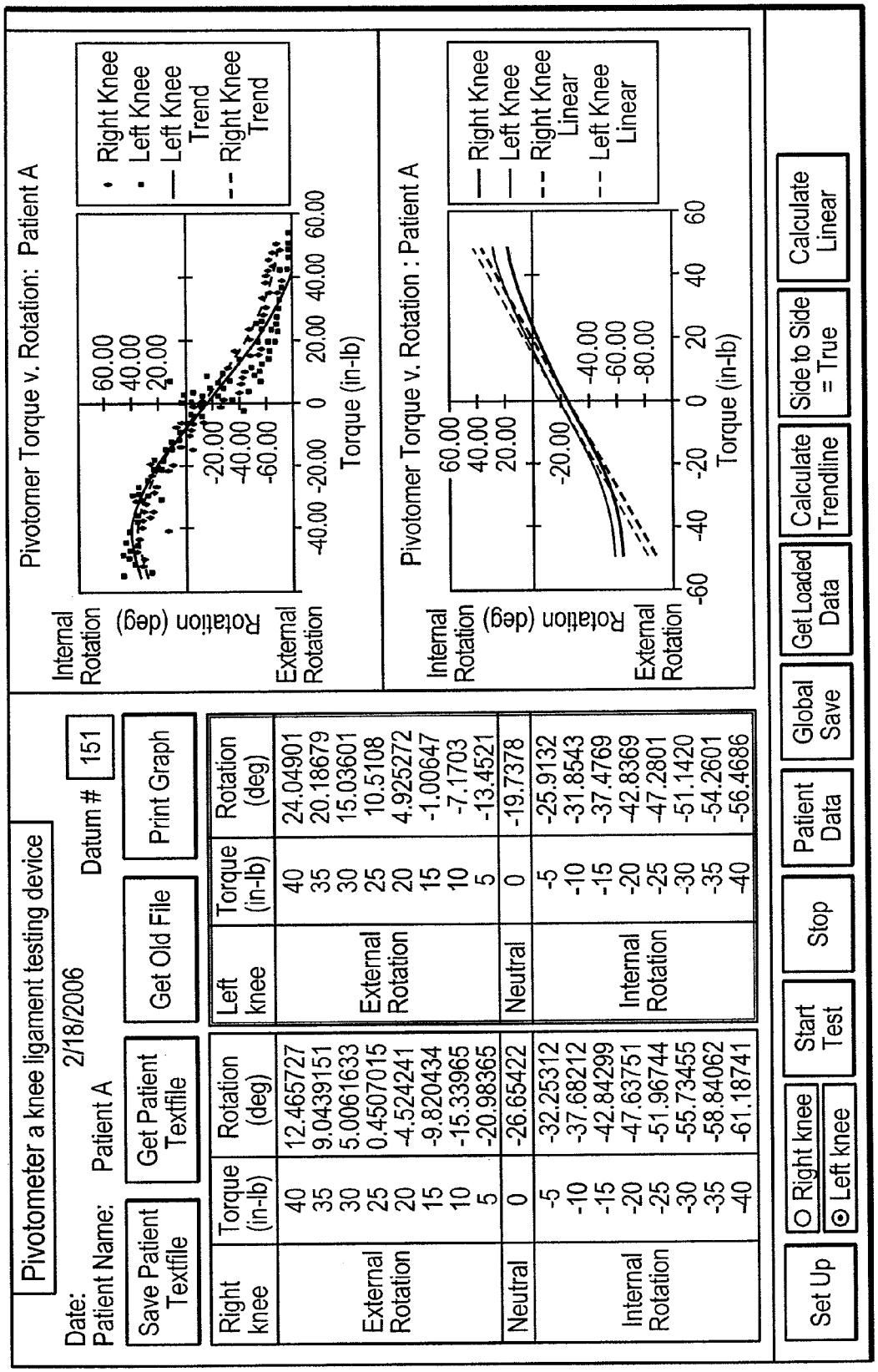

FIG. 19 is a screen shot of a data analysis tool in accordance with an embodiment of the present invention.

Figure 20:
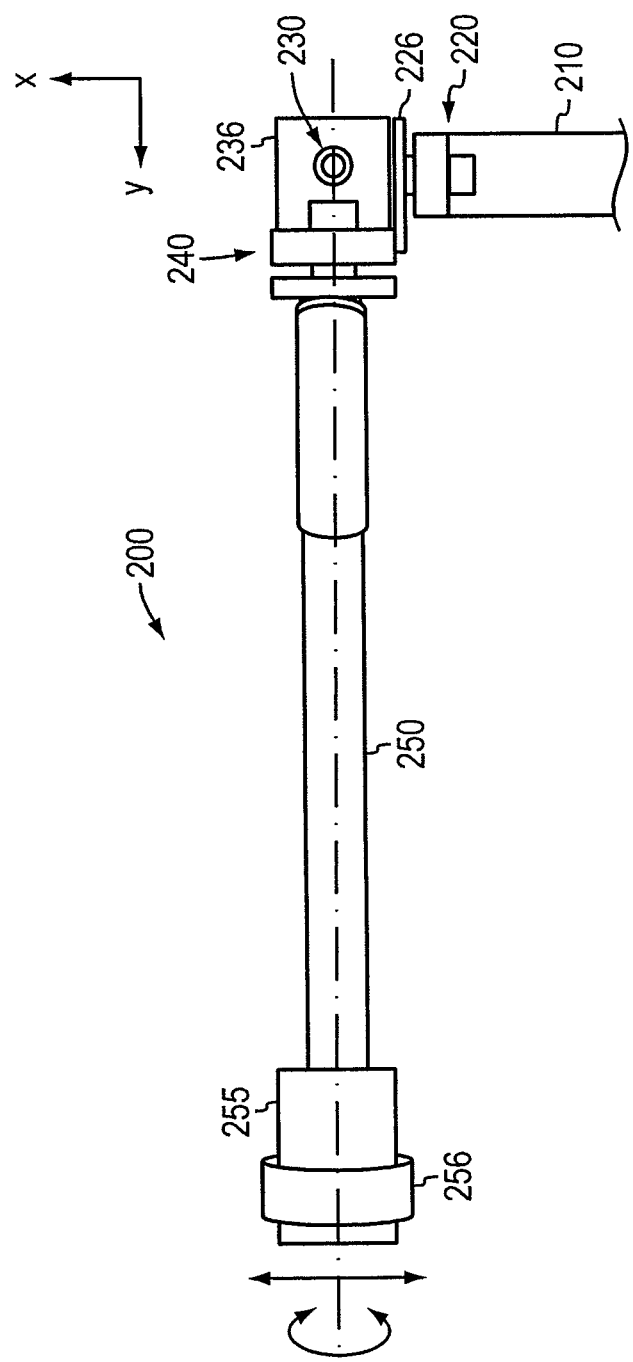

FIG. 20 is a drawing illustrating a top view of pivoting assembly 200 in accordance with an embodiment of the present invention.

Figure 21:
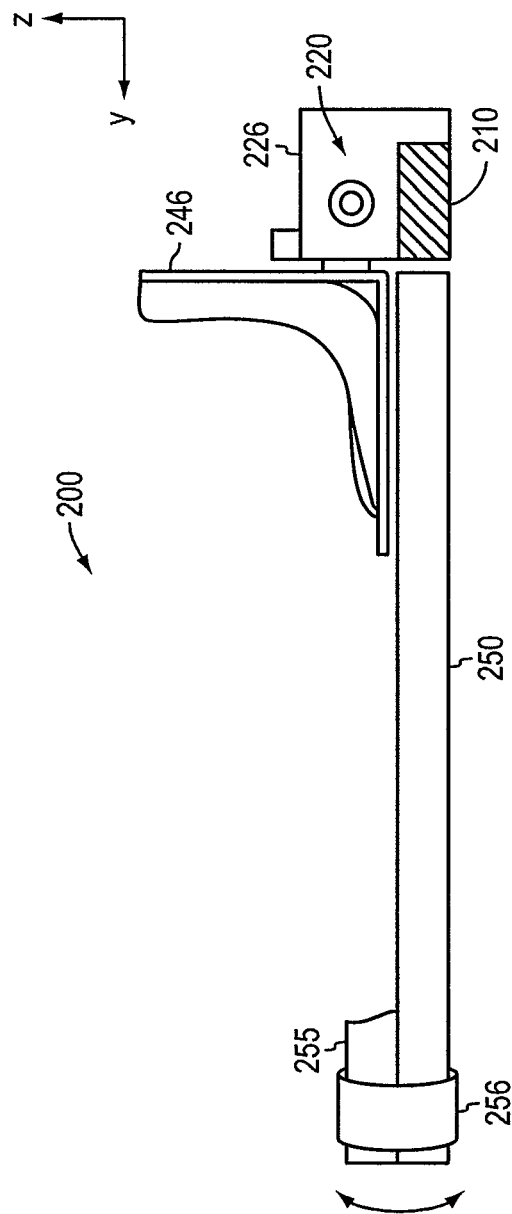

FIG. 21 is a drawing illustrating a side view of pivoting assembly 200 in accordance with an embodiment of the present invention.

Figure 22:
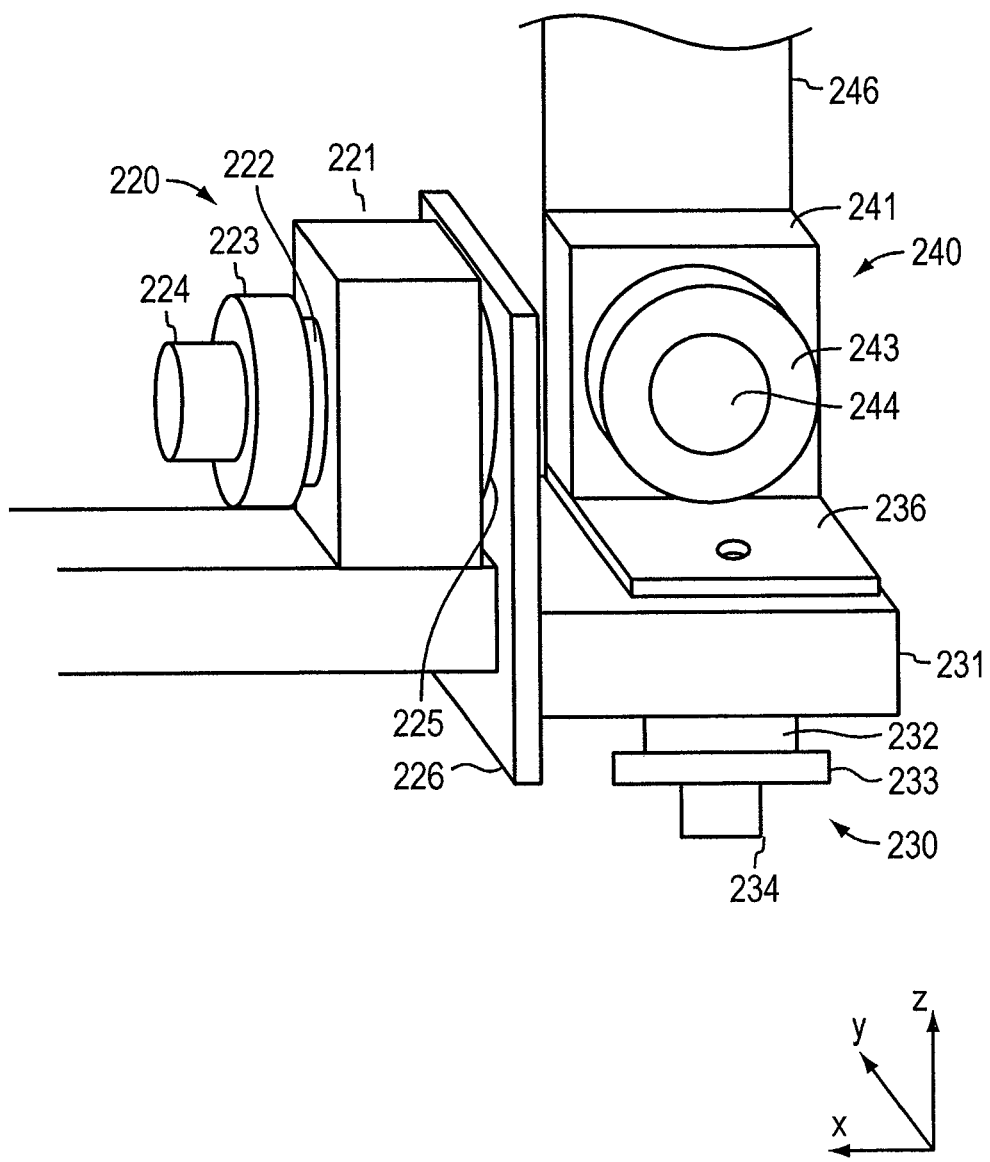

FIG. 22 is a drawing illustrating the multi-axis pivoting assembly 200 in accordance with an embodiment of the present invention.

Figure 23:
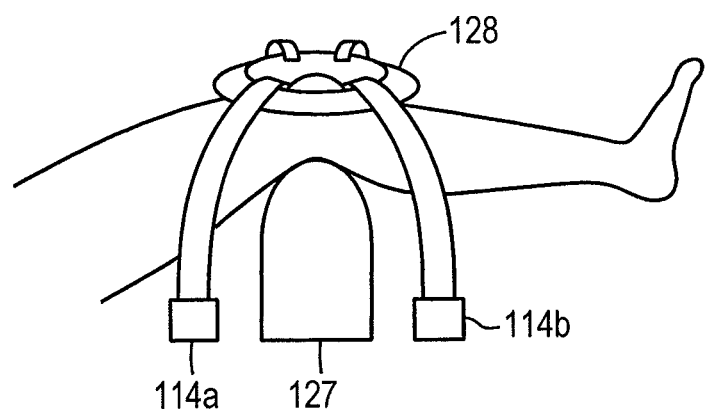

FIG. 23 is a drawing illustrating a torodial restraint for use with an embodiment of the present invention.

Figure 24:
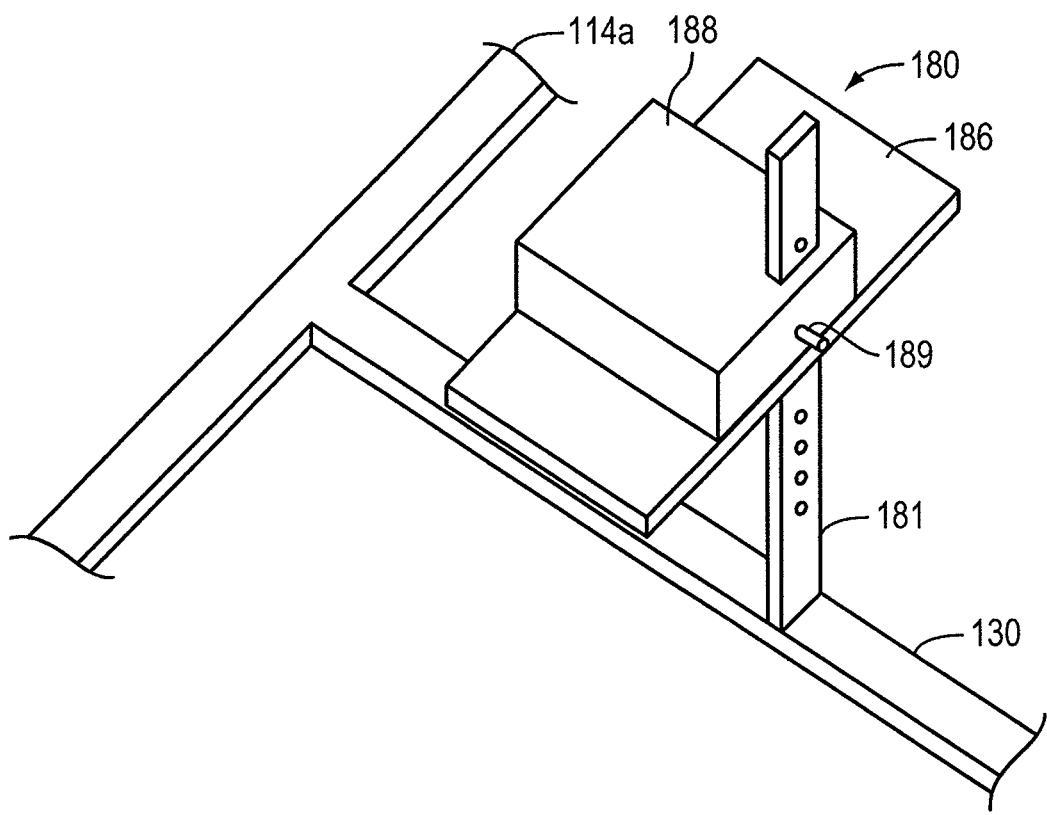

FIG. 24 is a drawing illustrating an adjustable thigh support 180, a spine 130 and a cross member 114a in accordance with an embodiment of the present invention.

Figure 25:
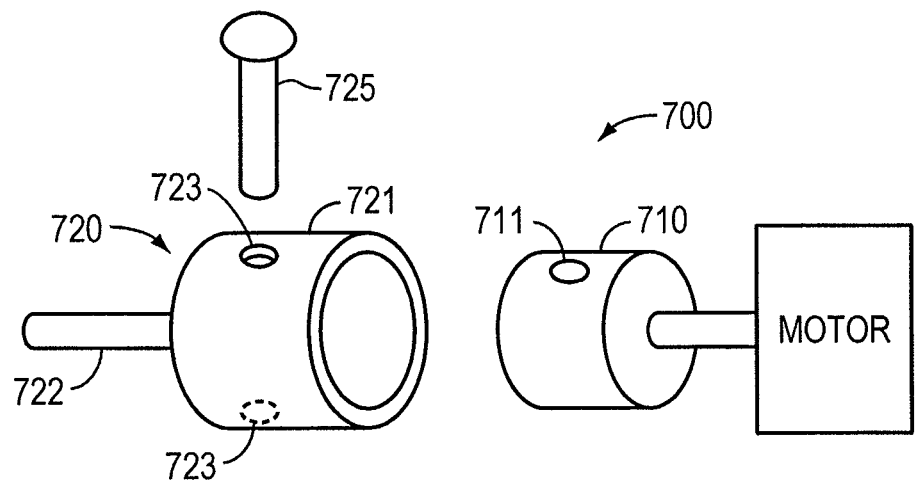
Figure 26:
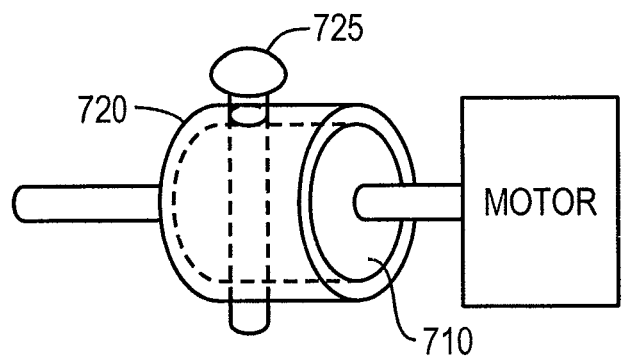

FIGS. 25 and 26 illustrate a breakaway coupling in accordance with an embodiment of the present invention.

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

General Construction and Operation

Generally described, embodiments of the present invention provide novel devices and methods to evaluate joints. More particularly, embodiments of the present invention provide a clinician with movement, "joint play" data for a joint to assist in diagnosing ligament damage or in evaluating the effectiveness of treatment for a damaged ligament. In the following paragraphs, an embodiment of the present invention will be described with relation to evaluating a knee joint; however, as one of ordinary skill in the art will appreciate, the concepts disclosed herein may be used to evaluate any other joints such as an elbow, shoulder and wrist.

The 'joint play' between the femur or thigh bone and the tibia or shin bone (and fibula) can be described by breaking down the motion into the usual six degrees of freedom. If the x-axis is situated such that it extends along the lateral to medial aspect of the right tibia, the y-axis should extend along the superior-inferior aspect of the right tibia and the z-axis should extend anterior-posterior in the right tibia as generally shown in FIGS. 1 and 2. Data related to four degrees of freedom may be useful in evaluating the joint play of the knee or tibia with respect to the femur. One of these degrees of freedom is rotation around the x-axis. This represents extension or straightening of the knee and flexion or bending of the knee to describe range of motion of the knee. The other three degrees of freedom are: rotation around the z-axis, rotation around the y-axis and translation at the z-axis.

Movement along these degrees of freedom stress the four primary ligaments in the knee which connect the thigh bone to the shin bones—the medial collateral ligament (MCL), the lateral collateral ligament (LCL), the posterior cruciate ligament (PCL) and the anterior cruciate ligament (ACL). The MCL is generally located on the side of the knee next to the other knee and connects the femur to the tibia. The LCL is generally located on the other side of the knee away from the other knee and connects the femur to the fibula (the fibula is directly connected to the tibia in the shin bone area). The ACL is generally located on the inside of the knee and connects between the femur and the tibia. The PCL is generally located on the posterior side of the knee and connects between the femur and the tibia.

Translation at the z-axis in the anterior direction stresses the ACL, while translation in the z-axis in the posterior direction stresses the PCL. Rotation at the z-axis in the right knee in the clockwise direction stresses the MCL and causes the tibia to rotate the knee into a 'knock knee' position, while rotation at the z-axis in the right knee in the counterclockwise direction stresses the LCL and causes the tibia to rotate into a 'bow legged' position.

Rotation about the y-axis represents a global measurement of the integrity of the knee including the shape of the femur as it sits into the shape of the proximal tibia, the presence or absence of the associated menisci within the knee, the integrity of the ligaments, and the integrity of the entire soft tissue sleeve of the knee.

The ACL is composed of three bundles, the posterolateral bundle (PLB), the intermediate bundle (IB), and the anteromedial bundle (AMB). Current research suggests that each of the bundles becomes stressed with anterior translation along the z-axis depending upon the position flexion or extension of the knee (rotation around the x-axis of the knee). The PLB is felt to control anterior translation along the z-axis while the knee is in or near full extension and the AMB is felt to control the anterior translation along the z-axis while the knee is in or near full flexion.

Embodiments of the present invention provide the clinician with apparatuses and methods to quantify the joint play for movement in one or a combination of the degrees of freedom discussed above. Using this data, a clinician can assess the integrity of the ligaments in the knee. Also, by comparing the data for a single patient against a larger population or comparing one knee to the other, abnormalities can be identified.

Tibia Rotation Embodiments

FIGS. 1-4 illustrate an embodiment of the present invention for gathering rotational data relating to a patient's lower leg to evaluate ligaments in the knee. It should be understood by those skilled in the art that concepts described below could be used to evaluate ligaments in the shoulder, elbow, wrist or any other joint.

Referring specifically to FIGS. 1 and 2, a patient 2 having two legs 3a,b with each leg having a thigh (or femur) 4, a knee 5, a shin (or tibia) 6, an ankle 7 and a foot 8 is positioned supine on a support surface such as a examining table or the floor. To minimize rotation at other joints of the leg, the patient's thighs 4 are extended upwardly and secured to a spacer 45. The patient's knee is bent to approximately 30 degrees of flexion; however it should be understood that the patient's legs could be flexed at any desired angle such as without limitation, 45 degrees, 60 degrees, 90 degrees or 120 degrees.

In the illustrated embodiment, both thighs 4 are secured to a spacer 45 using a strap 48. The spacer 45 is generally configured to hold the thighs 4 spaced apart such that the longitudinal axis if each tibia 6 is substantially aligned with the rotational axis of the ankle foot orthosis 57.

The patient's legs 3a,b are bent at the knee with the feet being secured into ankle foot orthosis ("AFO") using one or more straps (not shown). As will be understood by those skilled in the art, an AFO is a brace worn on the lower leg and foot to support the ankle, and it holds the foot and ankle in a desired position. In the illustrated embodiment, the AFOs are configured to pivot about an axis that is substantially parallel to the longitudinal axis of the patient's tibia 6. This arrangement contributes to more repeatable angular measurements because rotational movement is substantially isolated at the knee joint. The term AFO as used herein is to be interpreted broadly to include any known or developed device that restricts movement at the ankle such as an ankle brace or boot type structure.

Referring specifically to FIG. 3, internal ("I") and external rotation ("E") of the tibia (i.e. shin bone) can then be measured using instruments attached to the AFOs. These angular measurements can be taken with or without applying a known torque to the AFOs and therefore the tibia of the patient.

Exemplary Apparatus 10

Figure 5:
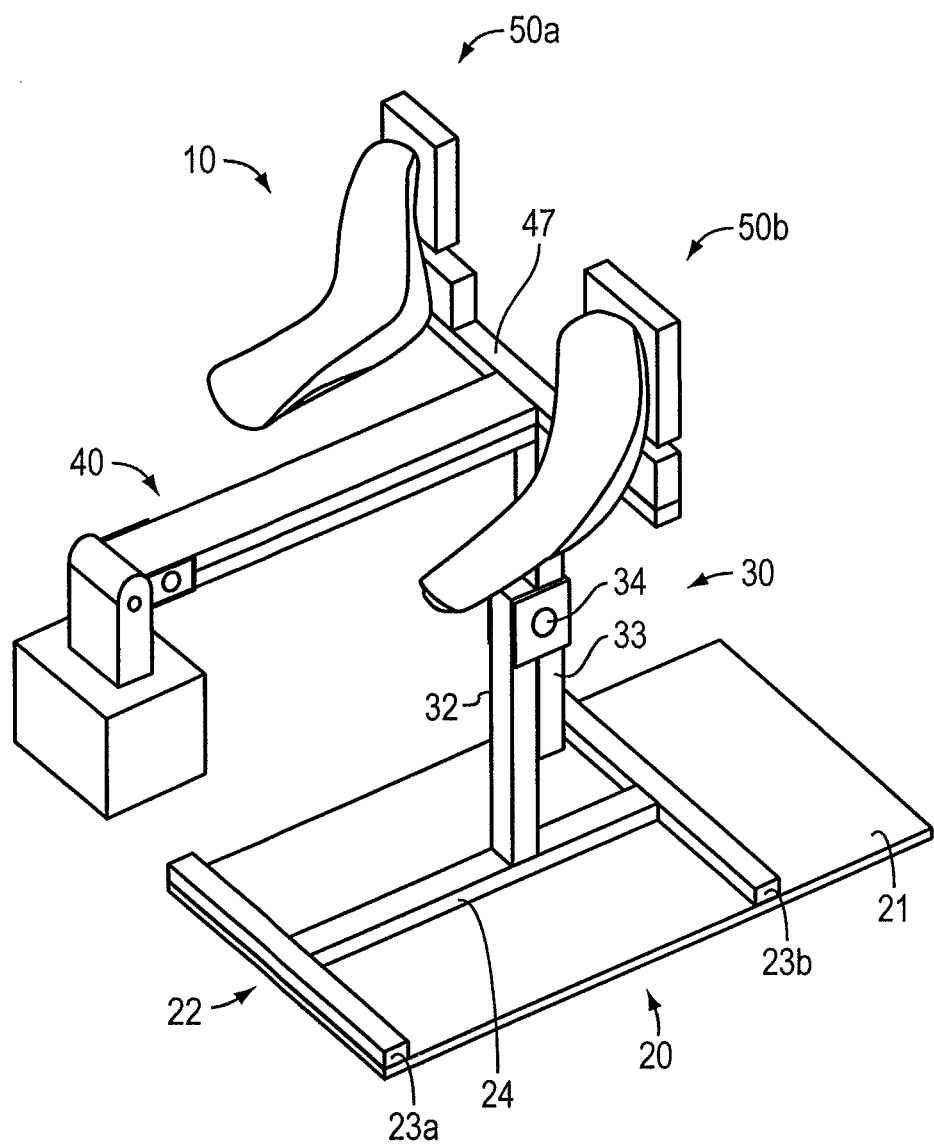
FIG. 5 is a drawing illustrating apparatus 10, which is an embodiment of the present invention.

An exemplary embodiment of the present invention, apparatus 10, is shown in FIG. 5. Generally described, apparatus 10 includes a base assembly 20, a support column 30, spacer support assembly 40, traverse member 47 and two rotating assemblies 50a, b.

The base assembly 20 is configured to be placed on a horizontal support surface such as an examining table or floor. In the illustrate embodiment, the weight of the device and friction between the base assembly 20 and the support surface provide stability to the device when in use. However, it should be understood that the stationary base assembly 20 may be secured to the support surface using straps, clamps, fasteners or any other securing means to provide additional stability.

This stationary base assembly 20 is substantially rigid and includes a base plate 21 and a substantially "H" shaped base frame assembly 22. The base plate 21 is substantially rectangular with an upper and lower surface. The lower surface is configured to be placed on a support surface and the base frame assembly 22 is rigidly attached to the upper surface.

The base frame assembly 22 includes two elongate members 23a,b that are spaced apart and substantially parallel. Intermediate the elongate members is a cross member 24 that is oriented substantially perpendicular to the elongate members and rigidly attached to the elongate members 23a,b near their midpoint. To increase rigidity, additional cross members 24 and elongate members 23 may be added. It should be understood that the base frame assembly 22 may be configured in any desirable shape such as for example a "T" shape, a triangle, a square, a rectangle, an octagon or a pentagon. Of course, the stationary base assembly may only include a base plate without the additional members or a base frame assembly without the base plate.

Extending up from the stationary base assembly 20 is the support column 30. The support column 30 is an elongate member extending upward substantially perpendicular from the cross member 24 of the stationary base assembly 20 and includes a stationary portion 32 and a sliding portion 33. The stationary portion 32 is rigidly attached to the cross member 24 of the stationary base assembly 20. To accommodate differing leg lengths between patients, the sliding portion 33 of the support column 30 may be slid along at least a portion of the length of the stationary portion 32 and releasably locked at desired location using locking knob 34 such that the overall length of the support column 30 is adjusted. Preferably, the height of the support column 30 is adjusted such that the patient's knees are flexed at approximately 30 degrees and the patient's tibias (or shins) are substantially parallel with the rotating axis of the pivoting assemblies 50a,b, which in this embodiment is substantially parallel with the support surface. It should be understood, however, that the support column 30 may be adjusted to any height desired by the clinician to gather a desired data set. Furthermore, as will be appreciated by those of skill in the art, the support column 30 of the present invention may be an elongate member without a length adjustment. In this case, the patient may be raised or lowered in relation to the structural base assembly to achieve the desired height.

Attached to one end of the adjustable support column 30 is the spacer support assembly 40. The spacer support assembly 40 positions a spacer between the thighs of a patient such that the thighs can be secured together. As will be discussed in greater detail below, securing the thighs of the patient reduces the influence of the femur on the measured rotation at the knee joint.

Figure 6:
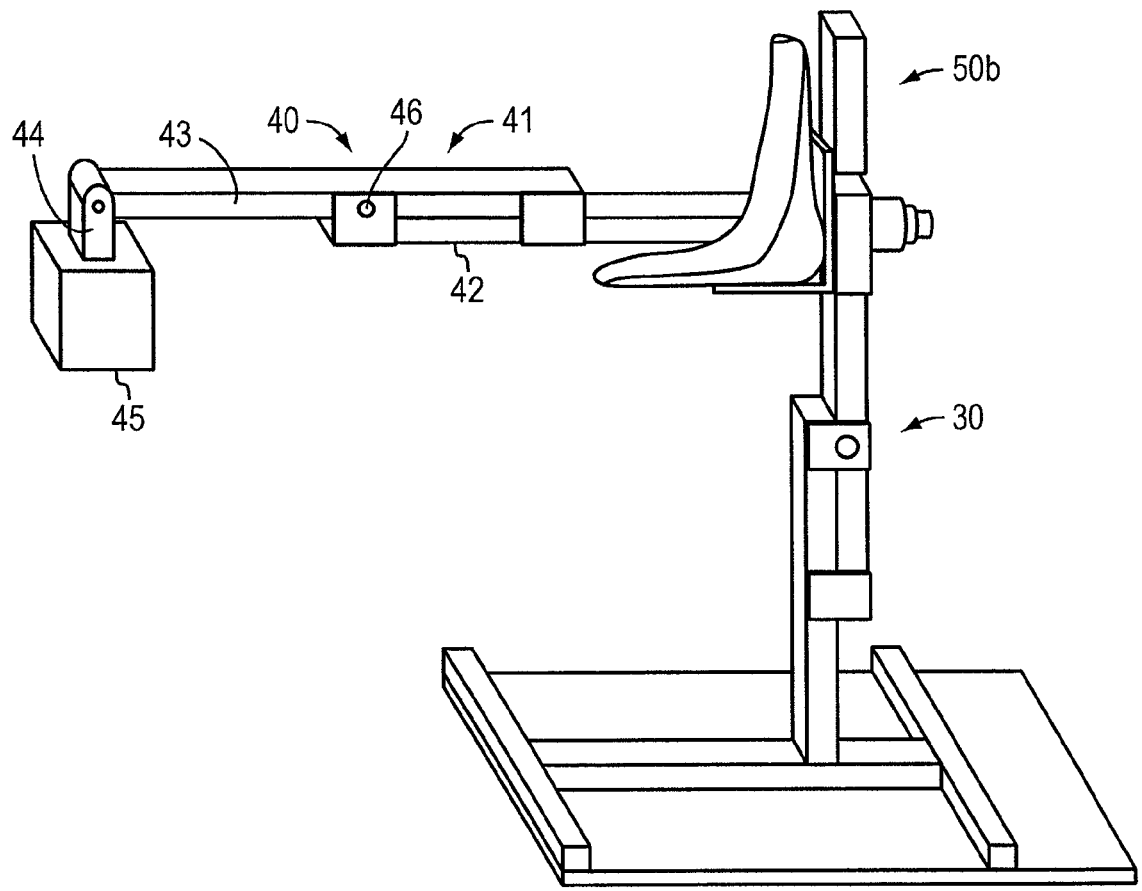
FIG. 6 is a drawing illustrating apparatus 10, which is an embodiment of the present invention. This view may be considered a side view of the apparatus 10.

Referring to FIG. 6, the spacer support assembly 40 includes a horizontal member 41, a spacer bar 44 and a spacer 45. The horizontal member 41 includes a stationary portion 42 and an adjusting portion 43. As with the support column 30, the horizontal member's length can be adjusted as desired by the clinician. The adjusting portion 43 slides along and extends out from the stationary portion 42 until the desired location of the spacer 45 is achieved. The adjusting portion 43 is then releasably secured to the stationary portion 42 using locking knobs 46. Of course, the horizontal member 41 may be elongate without a length adjustment. To facilitate discussion of the spacer support assembly 40, pivoting assembly 50a is not shown in FIG. 6.

Referring to FIGS. 5 and 6, the horizontal member's length and the support column's length are adjusted such that the patient's knee is bent at approximately 30 degrees and the patient's tibias are substantially aligned with the rotation axis of the pivoting assemblies 50a,b. However, a person of skill in the art will appreciate that these members may be adjusted as desired by the clinician to achieve a desired orientation Pivotably attached to the end of the horizontal member 41 is the spacer bar 44 as generally shown in FIG. 6. The spacer bar 44 pivots to allow the spacer 45 to be positioned intermediate the thighs of a patient. Alternatively, the spacer bar 44 may be rigidly attached to the horizontal member 41.

The spacer 45 is generally rectangular and preferably constructed of a foam type material such as polystyrene. A suitably sized recess is formed in the spacer 45 to receive one end of spacer bar 44. In use, the spacer 45 is positioned between the thighs of the patient near the knee joint and aids in aligning the tibia of the patient with the rotational axis of the associated pivoting assembly as will be discussed in greater detail later. To accommodate variations in thigh diameter between patients, spacers 45 of different sizes may be utilized. For example, a person with relatively small diameter thighs will require a larger spacer versus someone having relatively large diameter thighs in order to achieve the desired alignment.

Referring to FIG. 5, a transverse member 47 is also attached relative to the end of the support column 30. The traverse member 47 is elongate and provides support for the pivoting assemblies 50a,b, which will be discussed in greater detail later. The transverse member 47 is oriented substantially perpendicular to support column 30 and the horizontal member 41 and rigidly attached, proximate its midpoint, to the support column 30.

Pivoting Assemblies 50a, b

The apparatus 10 includes two pivoting assemblies 50a,b spaced apart and secured to the transverse member 47. The spacing between the pivoting assemblies provides clearance to rotate the assemblies. As one of ordinary skill in the art will appreciate, the spacing between the pivoting assemblies may be adjustable along the longitudinal length of the transverse member 47 such that the pivoting assemblies can be aligned with the natural spacing between the patient's feet.

Figure 7:
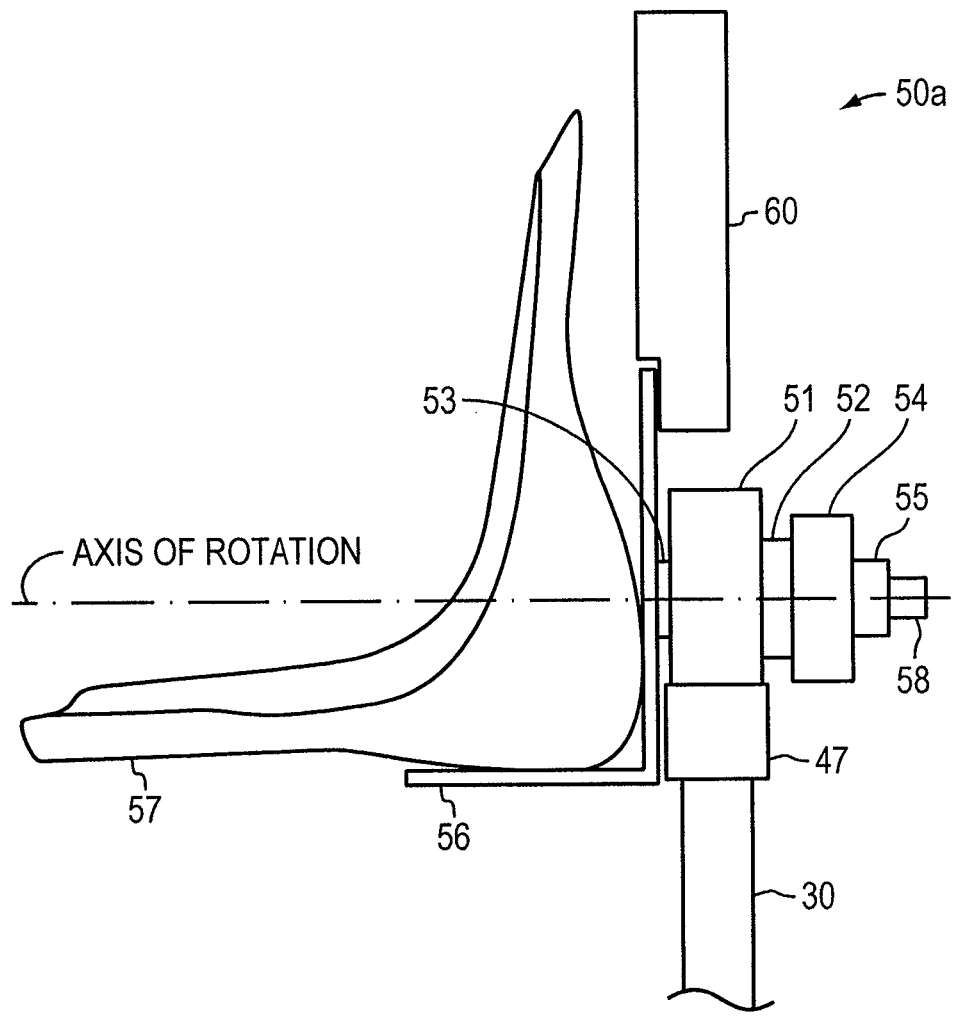
FIG. 7 is a drawing illustrating a portion of apparatus 10 including a pivoting assembly 50.

FIG. 7 illustrates details regard the construction of pivoting assembly 50a. Pivoting assembly 50b is configured the same as pivoting assembly 50a. Pivoting assembly 50a includes a bushing retainer 51, a bushing 52, a shaft 53, a collar 54, a socket 55, a conversion socket 58, an attachment bracket 56, an ankle-foot orthosis (AFO) 57 and an angle measuring device 60.

The pivoting assembly is attached to the transverse member 47 by a bushing retainer 51. The bushing retainer 51 is substantially rectangular with a suitably sized aperture configured to accept the bushing 52 such that the bushing does not rotate when inserted.

The bushing 52 is substantially cylindrical with a suitably sized aperture configured to accept the substantially cylindrical socket 55. As one of ordinary skill in the art will appreciate, the bushing 52 may be of any suitable material such as, without limitation, plastic, metal or aluminum. The bushing facilitates smooth rotational movement while restricting movement perpendicular to the axis of rotation. It should be understood that the bushing 52 may be replaced with a pin, needle or ball type bearing.

Referring to FIG. 8, the socket 55 has a cylindrical shape with a first end and a second end. In one embodiment, the first end includes a square aperture having an axis parallel with the longitudinal axis of the socket 55 and configured to facilitate the application of a torque to the pivoting assembly 50. The second end of the socket includes a hexagonal cavity that extends at least a portion of the elongate length of cylindrical socket 55. Socket 55 is similar to what is commonly referred to as a "deep well socket." The hexagonal cavity is configured to receive a first end of the shaft 53, which has a suitably sized hexagonal cross section. The shaft 53 is rigidly attached to the socket 55 using any known means such as without limitation adhesives or welding. In the illustrated embodiment, the second end of the shaft 53 extends beyond the second end of the socket 55; however, as will be understood by those of skill in the art, the second end of the shaft 53 may be flush with the second end of the socket 55 or recessed in the socket as desired.

As shown in FIGS. 7 and 9, the first end of the socket 55 extends out from the bushing 52, and a collar 54 is attached to the socket's outer diameter intermediate the socket's first end and the edge of the bushing 52. The collar 54 is secured to the socket using a set screw (not shown), and when secured, it resists axial movement of the socket 55 in the bushing 52.

Any type of torque applying device may be utilized with embodiments of the present invention. For example, a torque wrench may be used to engage the square aperture formed in the first end of the socket. In an alternative embodiment, a stepper motor is used to apply torque to the pivoting assembly. The stepper motor may be programmed to incrementally increase the rotation angle of the shaft until a predetermined torque is reached. With each incremental rotation, the torque is measured. The motor stops when a maximum torque threshold is reached. At this point, the angle may be captured. When using a stepper motor, it is advisable to also use a safety device such as clutch that disengages the motor when a predetermined maximum torque is reached.

In FIG. 25, an exemplary break away coupling is illustrated that may be used in connection with embodiments of the present invention. This coupling 700 includes an input shaft 710, an output shaft 720 and a pin 725. The input shaft 710 is substantially cylindrical and is attached to the drive shaft of a motor. The input shaft 710 defines a hole 711 passing through a portion of the input shaft. The output shaft 720 includes a first diameter portion 721 and a second diameter portion 722. The first diameter 721 portion defines a bore sized to accept the input shaft 710. The first diameter portion also defines two holes 723 sized and oriented to accept the breakaway pin 725. The second diameter portion 722 is configured to engage the socket. As will be understood by those of skill in the art, the holes in the output shaft and the holes in the input shaft align to receive the shaft and need not pass through the longitudinal axis of the shafts.

In use, the input shaft 710 is positioned inside the bore of the output shaft 720 and the breakaway pin 725 engages the holes defined by both the input and output shafts as generally shown in FIG. 26. This facilitates transfer of torque from the input shaft 710 to the output shaft 720. When the torque exceeds a predetermined threshold, the pin breaks allowing the input shaft 710 to spin freely. The breakaway pin 725 may be sized differently to achieve different breakaway torques or may be weaken with necked portion of notched portions to achieve differing torque thresholds as will be understood by those of skill in the art. This will allow a clinician to customize the threshold torque as desired.

As will be appreciated by those of skill in the art, other safety devices may also be used such as fuse or breakaway coupling.

In addition, it should also be understood that other types of motors may be used in connection with the present invention.

To facilitate use of different torque application devices, a conversion socket 58 may be used to facilitate connection to the socket. Conversion sockets are well known and allow, for example, a torque wrench with a ¼" protrusion to drive a socket with a ⅜" aperture. However, it should be understood that torque may be applied directly to the socket 55 without the use of a conversion socket if the torque device and the socket drive aperture (or protrusion) are suitably sized.

In an alternative embodiment, the shaft 53 has a circular cross section instead of hexagonal and the shaft diameter is suitably sized to cooperate with the bushing directly without the aid of the socket 55. To facilitate the application of torque, the end of the shaft may be configured with a recess sized to accept the protrusion of a torque application device or may include flats that may be engaged by a torque application device.

Returning to FIG. 7, the second end of the shaft 53 is rigidly attached to the attachment bracket 56, which itself is attached to an ankle-foot orthosis (AFO) 57. Thus, a torque is applied to the socket 55 or conversion socket 58 is transferred to the associated AFO 57 causing the AFO 57 to rotate.

Generally described, the AFO 57 is a brace that secures the lower leg and the foot of the patient thereby restricting movement of the ankle. As will be understood by those of skill in the art, the lower leg and the foot of the patient are preferably secured to the AFO using one or more straps. In the illustrated embodiment, the AFO holds the ankle in a neutral position (no plantar flexion); however, as will be appreciated by one of ordinary skill in the art, the AFO may be configured to hold the patient's foot in any angle desired by the clinician.

The attachment bracket 56 is generally "L" shaped with a first leg and a second leg. The first leg is secured to the lower leg portion of the AFO 57 while the second leg is secured to the foot portion of the AFO 57. Additionally, the second leg is also secured to the second end of the shaft 53. In use, the axis of rotation of the pivoting assembly 50 is generally aligned with the proximate location of longitudinal axis of patient's tibia.

Referring to FIGS. 7, 10 and 11, rotation angles or angular displacement are determined using the angle measuring device 60, which is secured to the second leg of the generally L shaped attachment bracket 56. As illustrated, the angle measurement device 60 is in substantial alignment with the centerline of the AFO; however as one of ordinary skill in the art will appreciate, the angle measurement device does not have to be aligned with the attachment bracket and AFO.

In the illustrated embodiment, the angle measuring device 60 indicates the rotation angle of the associated AFO with respect to gravity. These types of devices are often called inclinometers. Generally described, an inclinometer includes an arcuate scale having indicia of degrees (similar to a protractor) and a pointer that continually indicates the direction of gravity. As generally shown in FIG. 10, the arcuate scale rotates with the attachment bracket (and associated AFO), but the pointer continues to point in the direction of gravity. The resulting relationship between the pointer and the arcuate scale is the rotation angle with respect to gravity for the AFO. In should be understood that alternative methods of determining the angle of rotation may utilized in connection with the present invention such as, without limitation, digital levels, digital inclinometers, or potentiometers.

Preferably, the neutral position of the AFOs is in alignment with the support column 30 and the support column is aligned with the direction of gravity and therefore, the neutral position of the pivoting assemblies will register zero degrees on the angle measuring device 60. To verify the alignment of the support column, an angle measurement device may be secured to the support column itself. Using this angle measurement device in connection with conventional leveling techniques, the support column may be brought into alignment with the direction of gravity. Alternatively, the angle value taken from the angle measurement device on the support column can be used as an offset value for the angular measurements of the pivoting assemblies. In a further embodiment, the angle measurement devices on the pivoting assemblies themselves are used to determine an offset value. In this embodiment, the pivoting assemblies are placed in a neutral position and the resulting measurements on the angular measurement devices attached to the pivoting assemblies are used as an offset value as well. As one of ordinary skill in the art will appreciate, the angle measuring device 60 may be zeroed at neutral position.

Exemplary Apparatus 70 (Folding Apparatus 2)

FIG. 12 illustrates an alternative apparatus 70 that has the ability to collapse when not in use to facilitate transport and storage. Generally described, this embodiment employs a folding frame assembly 80 in place of the base frame 20 and support frame 30 as described with reference to apparatus 10. Specifically, the apparatus 70 includes a folding frame assembly 80, a spacer support assembly 40, a transverse member 47 and two pivoting assemblies 50*a,b*.

The folding frame assembly 80 includes a substantially "T" shaped base assembly 81, that is configured to be placed atop a support surface, two vertical supports 82*a,b* and a horizontal bar 83.

The vertical supports 82*a,b* are generally parallel to each other and are pivotably attached relative to the "T" shaped base assembly 81. A first vertical support 82*a* is attached to what could be referred to as the bottom of the "T" shaped base assembly while the second vertical support 82*b* is attached to what could be referred to as the top of the "T" shaped base assembly.

Plate brackets 84*a,b* are rigidly attached to the base assembly and restrict the pivoting action of the first vertical support 82*a*. Referring now to FIG. 13, a description of plate bracket 84*a* is provided. Plate bracket 84*a* is rigidly attached to base assembly 81. A pin 86, attached to the vertical support 82*a*, cooperates with an arcuate slot 85 defined by the plate bracket 84*a* to limit the pivoting action of vertical support 82*a* to substantially between 0 and 90 degrees. A locking pin ("P") secures the vertical support in a position substantially perpendicular to the plane defined by the base assembly 81. An aperture defined by the bracket 84*a* and a corresponding aperture defined by the vertical support 82*a* are aligned and suitably sized locking "P" is inserted into both apertures to lock the vertical support 82*a* into place. In alternative embodiments, a locking knob is attached to the pin 86 extending into the accurate slot such that the pivoting angle with respect to the base 81 may be secured at any angle substantially between 0 and 90 degrees. Plate bracket 84*b* is similar to plate bracket 84*a*.

Attached to the opposite ends of the vertical supports 82*a,b* is horizontal bar 83. This bar is pivotably attached to each of the vertical support members such that the vertical supports 82*a,b*, the base assembly 81 and the horizontal bar 83 form a rectangle. In alternative embodiments, the shape created by the connection of these four components is a parallelogram, or trapezoid.

Attachment of the horizontal bar 83 to the vertical support 82*b* is facilitated by plate brackets 84*c* and 84*d* (not shown). These brackets define an arcuate slot that cooperates with a pin attached to the horizontal bar 83 to restrict the pivoting action of the horizontal member as generally described with reference to FIG. 13.

Additionally, the plate brackets 84*c,d* and the horizontal bar 83 each define apertures that align when the relative orientation of the two members is substantially 90 degrees. The apertures are suitably sized to accept a locking pin (not shown), which secures the two members in a substantially 90 degree relationship, as generally described with reference to FIG. 13.

The spacer support assembly 40 is attached relative to the horizontal bar 83 such that the longitudinal axis of the spacer support assembly 40 is substantially parallel with the horizontal bar's longitudinal axis. The transverse member 47 and the pivoting assemblies 50*a,b* are configured the same as described earlier with reference to apparatus 10.

In the embodiment illustrated in FIGS. 12 and 14, the horizontal member 83 is not adjustable along its elongate axis; however, as one of skill in the art will appreciate, it could be adjustable as discussed with reference to apparatus 10.

When a data gathering session is complete, this embodiment of the present invention may be folded to a more compact size to facilitate transport and storage as generally illustrated in FIG. 14. The apparatus 70 may be collapsed by removing the locking pins (not shown) thereby allowing the vertical supports 82*a,b* to pivot together. In one embodiment, the apparatus 70 may be secured in the folded configuration using a locking pin and cooperating apertures in the plate brackets.

Referring briefly to FIG. 8, the footprint of the folded assembly may be further reduced by removing the pivoting assemblies 50*a,b* by loosening the set screw in the collar 54 and sliding the socket 55 and shaft 53 out of the bushing 54 towards the AFO 57.

Exemplary Apparatus 100

As with the preceding apparatus 10 and 70, apparatus 100 facilitates collection of rotational data with respect to a patient's tibia. FIG. 15 illustrates apparatus 100, which includes a frame assembly 110 and a pair of pivoting assemblies 150*a,b*. The pivoting assemblies 150*a,b* are configured similarly to those discussed with reference to FIG. 7. Frame assembly 110 is configured to support the pivoting assemblies 150*a,b* and position the patient to facilitate rotational data collection using the pivoting assemblies 150*a,b*.

FIGS. 16 and 17 illustrate a portion of a patient 2 and a portion of apparatus 100. Patient 2 is positioned supine on a support surface such as an examining table or the floor. The patient has two legs 3 with each leg having a thigh (or femur) 4, a knee 5, a shin (or tibia) 6, an ankle 7 and a foot 8. As illustrated, the patient's thighs are extended upwardly and positioned between a plurality of thigh positioning posts 120 and lower leg positioning posts 125, which restrict translational movement of the thigh 4 and lower leg 6. The thigh 4 may also be supported by thigh support 127. The patient's foot 8 is place in an AFO to facilitate rotation of the tibia.

Returning to FIG. 15 apparatus 100 includes a frame assembly 110 and two pivoting assemblies 150*a,b*. The components of the frame assembly 110 include two base plates 112*a,b*, two cross members 114*a,b*, a plurality of thigh positioning posts 120*a-d*, a plurality of lower leg positioning posts 125*a-d*, a spine member 130, a carriage 135 and a traverse member 140. The two substantially rectangular base plates 112*a,b* are space apart and oriented within substantially the same plane. The based plates 112*a,b* have a lower surface configure to rest atop a supporting surface. As one of ordinary skill in the art will appreciate, the base plates may be fastened to a support surface using fasteners, straps, clamps or other fastening means. Attached to the upper surface of the base plates are the two parallel and substantially elongate cross members 114*a,b*. These cross members 114*a,b* provide a mounting surface for a desired number of positioning posts.

In the illustrated embodiment, cross member 114*a* supports four thigh positioning posts 120*a-d*. As illustrated, the thigh positioning posts 120*a-d* are oriented substantially perpendicular to the cross member 114*a*. The thigh positioning posts 120*a-d* are connected to the cross member 114*a* such that their location may be adjusted and locked at desired locations along the length the cross member 114*a*. In use, a patient is positioned into apparatus 100 with their lower thigh proximate the thigh positioning posts 120*a-d*. The thigh positioning posts 120*a-d* are adjusted to restrict movement of the thighs in a plane substantially perpendicular to the longitudinal axis of the patient's femur. For example, thigh positioning post 120*a* and thigh positioning post 120*b* are space apart to receive a patient's thigh. One or both of the thigh positioning posts 120*a-b* are then urged against the patient's thigh and locked in place. The same procedure may be used for thigh positioning posts 120*c-d* with respect to the patient's other thigh.

Similar to the thigh positioning posts 120*a-d*, in the illustrated embodiment also includes four lower leg positioning posts 125*a-d*. These posts are connected to the cross member 114*b* such that their location may be adjusted and locked at desired locations along the length cross member 114*b*. When a patient is positioned in apparatus 100, the lower leg positioning posts 125*a-d* are located just below the knee to restrict translational movement of the tibia.

In one embodiment, a strap (not shown) is provided proximate cross member 114*a* to further restrict movement of the patient's thighs. This strap may be connected relative to cross member 114*a* such that when tightened, the thighs are urged toward the cross member 114*a*. In one embodiment, a single strap is used to secure both thighs. Alternatively, one strap for each thigh may be employed. Other embodiments may not include this strap.

In an alternative embodiment, a thigh anterior support member 122 may be removeably secured to the thigh positioning posts 120*a-d* after positioning the patient's thighs between associated thigh positioning posts. The thigh anterior support member 122 may be urged against the top of the thigh and locked into place. In one embodiment, the thigh support bar is sized to extend towards the hip as generally shown in FIGS. 16 and 17. The thigh anterior support member 122 may also extend toward the knee and contact the knee proximate the patella. In a further embodiment, the thigh anterior support member is a bar attached to the thigh positioning posts.

In one embodiment, a thigh support 127 may be positioned intermediate cross member 114*a* and 114*b*. The thigh support 127 is positioned beneath the thigh of a patient in use and aids in achieving the desired angle between the patient's thigh and the supporting surface. The thigh support 127 may be padded for additional comfort.

Referring to FIG. 23, a torodial restraint 128 may be used to further secure the patient's leg. The torodial restraint is positioned proximate the patella of the knee and attached to the cross members 114a,b using straps 129.

Referring now to FIG. 24, a further embodiment may include an adjustable thigh support 180. As illustrated, the adjustable thigh support 180 is attached relative to the spine 130 and is configured to support the underside of the patient's thighs. The adjustable thigh support 180 includes a support rod 181, a thigh platform 186, a separator 188 and a pin 189. The support rod 181 is attached to and extends substantially perpendicularly from the spine 130. The support rod 181 defines a plurality of holes 182 space apart along a portion of the length of the support rod. The holes 182 are suitably sized to accept a locking pin 189.

The platform 186 is a substantially flat member with the separator 188 attached to its upper surface. In use, a patient's thighs are positioned atop the platform 186 and are spaced apart by the separator 188. The height of the platform and separator assembly above the spine 130 may be adjusted by selectively engaging the locking pin 189 with a suitably size hole defined by the separator 186 and one of the holes 182 in the support rod.

Although the adjustable thigh support 180 is illustrated with an embodiment having a single cross member 114a, one of skill in the art will recognize that this support may be used with embodiments having both cross member 114a and 114b. In this case, the adjustable thigh support would be positioned intermediate cross member 114a and 114b.

Attached proximate the center of the cross member 114b is one end of the substantially elongate spine 130. The spine 130 is oriented substantially perpendicular to the cross member 114b and provides support for the carriage 135. The carriage 135 is adjustable and lockable using locking member 132 along at least a portion of the length of the spine 130. In use, the carriage 135 is adjusted along the length of the spine 130 as desired to accommodate differing leg lengths between individual patients and to achieve the desired knee flexion.

In an alternative embodiment, the spine 130 is attached to cross bar 114a and does not include a second cross bar 114b or base plates 112a,b.

Transverse member 140 is attached to the carriage b and supports two pivoting assemblies 150a,b, which is similar to the transverse member 47 discussed with reference to apparatus 10. The proximate midpoint of the transverse member 140 is attached to carriage 135 and one of the pivoting assemblies 150a,b is attached proximate each end of the substantially elongate transverse member 140. The pivoting assemblies 150a,b are configured similar to pivoting assembly 50a as described with reference to FIG. 7. Apparatus 100 may also include angle measurement devices as generally described with respect to apparatus 10.

Referring to FIGS. 15 and 16, the carriage 135 orients the transverse member 140 such that the pivoting assemblies 150a,b are held at an angle that facilitates positioning of the patient's knee with approximately 30 degrees of flexion. In one embodiment, the pivoting assemblies 50a,b are held at a 15 degree angle with respect to the support surface. One skilled in the art will appreciate that the pivoting assemblies may be positioned at any desired angle to achieve a desired degree of knee flexion.

Method of Use

As previously discussed, embodiments of the present invention measure the limb rotation in response to a torque for the purpose of diagnosing ligament damage and also to determine the effectiveness of ligament treatment. Although concepts embodied in the present invention may be used to measure rotation at any joint, the following discussion will focus on measuring rotation at a knee joint.

To provide accurate internal and external rotation measurements for the knee joint, the influence of the other joints of the leg need to be minimized. Embodiments of the present invention restrict the motion of the other joints associated with the leg such that accurate knee rotation measurements can be taken.

Referring to FIG. 18, the method begins at Step 500 where the patient is positioned in a supine position with their knees bent and each foot secured to a pivoting assembly. In one embodiment, apparatus 10 is positioned on a horizontal support surface and the patient is positioned on their back with the spacer support assembly intermediate the patient's thighs and each of the patient's feet are positioned in an associated AFO. In one embodiment, the patient's feet are secured individually to their associated AFOs using straps around both the lower leg and the foot. In this way, the ankles are substantially immobilized thereby minimizing any influence of the ankle joints on the rotational measurements.

When using apparatus 10, the lengths of the horizontal member 41 and the support column 30 are adjusted for proper alignment of the legs. Preferably, the lengths are adjusted such that the patient's knees are bent at approximately 30 degrees and the patient's shins (or tibias) are substantially aligned with the pivoting assemblies. This arrangement helps to minimize rotation of the thigh when the AFOs are rotated. However, the flexibility of an individual patient may not permit this alignment, and therefore, the device can accommodate legs in other configurations or flexion angles.

At Step 505, the patient's thighs are secured to minimize the influence of the femur on the rotational measurements. With apparatus 10, a suitably sized space is positioned on the spacer bar 44. A strap is then tightened around the patient's thighs proximate the spacer 45 such that the thighs are urged together and into contact with the spacer.

After securing the patient to the device, rotational measurements can be taken for a first leg at Step 510. In one embodiment, a predetermined force is applied in a first direction (e.g., clockwise) and an angle measurement is taken. Then, a predetermined force is applied in a second direction (e.g., counter-clockwise) and an angle measurement taken. This procedure may then be repeated for a second leg at Step 515. A typical applied torque may be 50 inch-pounds; however, any torque desired by the clinician may be applied using embodiments of the present invention.

In an alternative embodiment, a clinician oscillates the pivoting assembly from a predetermined torque in a first direction and then to a predetermined torque in a second direction. The torques for the two directions may or may not be the same. Torque readings and angle readings may be taken at predetermined angles, torques or other criteria for later analysis.

In one embodiment, an analysis tool is utilized to capture torque and angle readings at predetermined time intervals as the clinician oscillates the pivoting assembly. FIG. 19 provides a screen shot of an exemplary analysis tool that may be used in connection with the present invention. When the clinician is ready to collect data, the clinician selects the appropriate knee and actuates the start test button on the screen. Then, the clinician oscillates the pivoting assembly between internal rotation and external rotation to a desired torque using a torque application device (e.g., torque wrench or stepper motor). In one embodiment, the clinician rotates the pivoting assembly clockwise until a torque reading of 40 in-lbs is reached and then rotates the pivoting assembly counter-clockwise until a torque reading of 40 in-lbs is reached.

Meanwhile, torque and angular displacement readings are captured by the analysis tool at predetermined intervals, such as every 50 milliseconds, as the clinician oscillates the pivoting assembly. When a predetermined number of data points are captured, the computer signals that data collection is complete. At which point, the clinician may repeat the data capture procedure for the opposite leg.

In one embodiment, the analysis tool plots the raw data onto a graph and determines a best fit equation for the raw data. This can be seen in the upper graph in FIG. 19. The lower graph shows two lines associated with the best fit equation, one for each knee. Also provided in the lower graph is a slope estimation for the best fit equations.

At Step 520, comparisons are made between the first knee and the second knee to evaluate relative performance. Assume a patient is experiencing pain in the first knee. The clinician can focus in on discrepancies between the angular measurements of the two knees to aid in diagnosing the cause of the pain. Furthermore, if treatment has already been performed and a significant discrepancy remains, additional treatment may be necessary.

When using the analysis tool, the clinician can determine from the lower graph the neutral angular position of the patient's knees, which is represented by the point where the best fit equation crosses the torque axis. Or in other words, where the torque value is zero. Furthermore, the slope of the line gives an indication of the "looseness" in the knee. Discrepancies between the neutral angular position and the slope can indicate an abnormal situation that may require surgery or other treatment.

Although the above method was described with reference to apparatus 10, the method is equally effective when used in connection with apparatus 70 and apparatus 100.

For apparatus 70, the base assembly 80 is positioned on a support surface with the two vertical supports substantially perpendicular to the support surface. The patient is then positioned in the apparatus with the vertical supports between the patient's thighs and each foot is secured to a pivot assembly. A strap is then tightened against the patient thigh such that they are urged into contact with the spacer. Data may then be gathered as generally described above.

When data gathering is complete and the patient removed from the apparatus 70, the locking pins may be disengaged and the apparatus folded to facilitate storage.

When the method is performed using apparatus 100, each of patient's thighs are positioned between two thigh positioning posts and two lower leg positioning posts. The patient's feet are then secured to pivoting assemblies. Next, the thigh positioning posts and the lower leg positioning posts are adjusted to restrict motion of the leg proximate the posts. In one embodiment, a thigh support bar is also urged against the top of the thigh proximate the thigh positioning posts. In another embodiment, a strap is tightened proximate the thigh support posts to provide additional restriction of the thigh during measurement. A torodial restrain may also be employed. One of skill in the art will recognize that any of these restraint techniques either alone or in combination may be used in connection with embodiments of the present invention.

Once the patient is secured to apparatus 100, measurements may be taken as generally described with reference to apparatus 10 above.

Multi-Axis Embodiments

In previously described apparatuses, rotational movement of the tibia about the longitudinal axis of the tibia was evaluated. In an alternative embodiment, a multi-axis pivoting assembly 200 is used in place of pivoting assemblies 50 and 150 in the previously described apparatus. Multi-axis pivoting assembly 200 provides two additional movements of the tibia that may be evaluated to obtain a more complete evaluation of the performance of ligaments in the knee.

FIGS. 20 and 21 provide a top and side view, respectively, of multi-axis pivoting assembly 200 attached to a transverse member 210. Transverse member 210 is similar to transverse members 47 and 140. Multi-axis pivoting assembly 200 includes a first pivoting assembly 220, a second pivoting assembly 230, a third pivoting assembly 240, a lifting bar 250 and a lower leg cuff 255.

The first pivoting assembly 220 facilitates evaluation of translational movement of the proximal end of the tibia in a plane substantially parallel to the y-z plane as shown in FIGS. 21 and 22. In other words, the first pivoting assembly 220 evaluates relative movement of the tibia in a substantially sagittal plane. The first pivoting assembly 220 facilitates this movement by pivoting about an axis substantially parallel with the "x" axis as shown. First pivoting assembly 220 includes a bushing retainer 221, a bushing 222, a collar 223, a socket 224 and a shaft 225 in the same relative arrangement as discussed in relation to the pivoting assembly 50a and FIG. 7. However, the shaft 225 is attached to plate bracket 226 instead of attachment bracket 56, as described with reference to pivoting assembly 50a, such that when the shaft rotates, the plate bracket 226 rotates. First pivoting assembly 220 also includes a locking pin (not shown) that is configure to selectively engage a suitably sized hole in the attachment plate 226 to prevent the first pivoting assembly 220 from rotating.

The second pivoting assembly 230 facilitates evaluation of translation movement of the proximal end of the tibia in a plane substantially parallel with the x-y plane as generally shown in FIGS. 20 and 22. In other words, the second pivoting assembly 230 evaluates relative movement of the tibia in a substantially coronal plane. The second pivoting assembly is rigidly attached to plate bracket 226. The second pivoting assembly 230 includes a bushing retainer 231, a bushing 232, a collar 233, a socket 234 and a shaft (not shown) in the same general arrangement as discussed with regard to pivot assembly 50a and FIG. 7. The bushing retainer 231 is rigidly attached to the plate bracket 226. Similar to the first pivoting assembly 220, the shaft of the second pivoting assembly 230 is attached to a plate bracket 236, which is oriented within a plane substantially parallel with the "z" axis. Furthermore, the second pivoting assembly 230 includes a locking pin (not shown) that selectively engages a suitably sized hole formed in the plate bracket 236 to prevent rotation of the second pivoting assembly as desired.

Referring to FIG. 22, the third pivoting assembly 240 is attached to the plate bracket 236 is. The third pivoting assembly 240 facilitates evaluation of rotation movement of the tibia substantially about its longitudinal axis (i.e., substantially parallel with the "y" axis). This assembly includes a bushing retainer 241, a bushing (not shown), a collar 243, a socket 244 and a shaft (not shown) in the same general arrangement as discussed in relation to the pivoting assembly 50a and FIG. 7. The shaft is attached to an attachment bracket 246.

Returning to FIGS. 20 and 21, the lifting bar 250 is substantially elongate and attached to the pivot assembly 240 at one end. Attached to the opposite end is the lower leg cuff 255 with an associated strap 256. To accommodate different leg lengths, the lifting bar B may have an adjustable length. Generally described, the lifting bar 250 applies a force near the knee when the first pivoting assembly 220 or the second pivoting assembly 230 is engaged. For example, when the first pivoting assembly 220 is engaged and rotated, the two plate brackets 226 and 236 are also rotated causing the lifting bar to pivot. This pivoting action causes a force proximate the lower leg cuff under the lower leg proximate the knee.

Although the illustrated multi-axis pivoting assembly 200 includes three individual pivot assemblies, one of skill in the art will appreciate that other embodiments of the present invention may include a single pivoting assembly or any combination of the three pivoting assemblies described above.

Methods of Use for the Multi-Axis Pivot Assembly 200

As discussed above, the multi-axis pivoting assembly 200 allows a clinician to evaluate the performance of a knee in three different degrees of freedom. The following paragraphs will generally describe evaluating ligaments in the knee using the three different pivoting assemblies of the multi-axis pivoting assembly. It should be understood that a clinician may desire to only use one or two of the possible three pivoting assemblies to evaluate the knee.

Before evaluating knee ligaments using the multi-axis pivot assembly 200, the patient is place in either apparatus 10, 70 or 100. Of course, the pivoting assemblies 50a,b in those devices would be replace with the multi-axis pivot assembly 200. With each apparatus, the patient's feet are placed in the AFOs and their thighs are secured to the apparatus. In addition, the patient's lower leg is secured to the lower leg cuff.

To evaluate the translational movement of the tibia in a direction substantially parallel with the y-z plane, the locking pin in the first pivoting assembly 220 is disengaged and the locking pin in the second pivoting assembly 230 is engaged. At this point, a torque is applied to the first pivoting assembly 220 causing the AFO and lifting bar 250 to pivot as well. This pivoting action causes a force to be applied proximate the lower leg cuff 255 causing the proximal end of the tibia to move in relation to the femur.

The amount of linear movement of the tibia may be determined in a variety of ways. For example, an inclinometer may be applied to the lifting bar 250 or the patient's lower leg to determine the angle of the patient's tibia with respect to the direction of gravity at differing torques. Using this data, the angular displacement can be calculated with regard to the length of the lifting bar 250. In another embodiment, the rotation angle of the first pivoting assembly is measured using a potentiometer or other angular displacement measuring device. Of course a linear displacement sensor may be placed proximate the tibia near the knee to manually or automatically measure the linear displacement of the tibia in response to the applied force with respect to the femur or other reference frame.

For evaluation purposes, the linear displacement may be evaluated with regard to torque applied or the torque applied may be converted to a force at the end of the lifting bar 250 if desired.

To evaluate the translational displacement in a plane substantially parallel with the x-y plane in response to a given force, the locking pin of the first pivoting assembly 220 is engaged such that it does not pivot and the locking pin of the second pivoting assembly 230 is disengaged to allow pivoting. Next, a torque is applied to the second pivoting assembly 230 thereby causing a force to be applied at the knee in a direction substantially parallel with the "x" axis. To determine the displacement of the tibia proximate the knee, the angular displacement of the pivoting assembly may be measured using a potentiometer or other angular displacement measuring device. This angular measurement result may then be translated to a linear distance using the length of the lifting bar if desired. Alternatively, the linear displacement may be measured manually or automatically using a linear displacement sensor or other measuring device with reference to the femur or other reference frame. In one embodiment, linear displacement data is gathered for different force values or torque values to determine the performance of the ligaments in the knee.

Finally, to evaluate the rotational performance of the knee in response to a torque applied about the longitudinal axis of the tibia, the locking pins of both the first pivoting assembly 220 and second pivoting assembly 230 are engaged thereby preventing pivoting of the first and second pivoting assemblies 220, 230, respectively. Next, a torque is applied to the third pivoting assembly as generally described with relation to apparatus 10, 70 and 100.

CONCLUSION

In concluding the detailed description, it should be noted that it would be obvious to those skilled in the art that many variations and modifications can be made to the preferred embodiments without substantially departing from the principles of the present invention. Also, such variations and modifications are intended to be included herein within the scope of the present invention as set forth in the appended claims. Further, in the claims hereafter, the structures, materials, acts and equivalents of all means or step-plus function elements are intended to include any structure, materials or acts for performing their cited functions.

It should be emphasized that the above-described embodiments of the present invention, particularly any "preferred embodiments" are merely possible examples of the implementations, merely set forth for a clear understanding of the principles of the invention. Any variations and modifications may be made to the above-described embodiments of the invention without departing substantially from the spirit of the principles of the invention. All such modifications and variations are intended to be included herein within the scope of the disclosure and present invention and protected by the following claims.

That which is claimed:

1. An apparatus for evaluating the performance of the knee of a patient's leg in multiple degrees of freedom, said patient having a femur, a knee, a tibia, an ankle and a foot, said apparatus comprising:
   A) a frame;
   B) a device for securing said femur of said patient relative to said frame;
   C) a foot accepting element configured to detachably receive and secure at least a portion of the foot such that force can be transferred from said foot accepting element through said foot to said tibia;
   D) a multi-axis pivoting assembly attached intermediate said foot accepting element and said frame, said multi-axis pivoting assembly configured to facilitate multi-axis pivoting of said foot accepting element relative to said frame and said multi-axis pivoting assembly itself comprising:
1) a first pivot subassembly configured to transfer a first torque to said tibia causing movement of said tibia relative to said femur in a first degree of freedom, wherein said first pivot subassembly includes first and second portions having a pivotable connection therebetween along a first pivot axis, wherein said first pivot axis lies in a plane which is further distal than the entirety of the foot of said patient than is said foot accepting element in use, said distal relationship being relative to the leg of the patient; and
2) a second pivot subassembly configured to transfer a second torque to said tibia causing movement of said tibia relative to said femur in a second degree of freedom, wherein said second pivot subassembly includes first and second portions having a pivotable connection therebetween along a second pivot axis; wherein said second pivot axis is at an angle relative to said first pivot axis and is configured to provide a torque about the longitudinal axis of said tibia of said patient in use;
E) a first angle measuring device configured to measure angular displacement of said first pivot subassembly in response to said first torque; and
F) a second angle measuring device configured to measure angular displacement of said second pivot subassembly in response to said second torque.

2. The apparatus as claimed in claim 1, wherein said first and second pivot subassemblies are selectively independently lockable such that one of said subassemblies does not undergo pivoting while the other is undergoing pivoting.

* * * * *